United States Patent
Potta et al.

(10) Patent No.: US 10,973,781 B2
(45) Date of Patent: *Apr. 13, 2021

(54) EPINEPHRINE SPRAY FORMULATIONS

(71) Applicant: Hikma Pharmaceuticals USA Inc., Eatontown, NJ (US)

(72) Inventors: Thrimoorthy Potta, Phoenix, AZ (US); Craig Bastian, Gilbert, AZ (US); Ningxin Yan, Chandler, AZ (US); Venkat Goskonda, Phoenix, AZ (US); Chandeshwari Chilampalli, Chandler, AZ (US); Rachana Inavolu, Chandler, AZ (US); Eshwaran Narayanan, Chandler, AZ (US)

(73) Assignee: HIKMA PHARMACEUTICALS USA INC., Eatontown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,853

(22) Filed: Mar. 1, 2019

(65) Prior Publication Data

US 2019/0216750 A1 Jul. 18, 2019

Related U.S. Application Data

(63) Continuation-in-part of application No. 16/240,632, filed on Jan. 4, 2019, which is a continuation-in-part of application No. 16/023,313, filed on Jun. 29, 2018, now Pat. No. 10,617,637, which is a continuation-in-part of application No. 16/007,998, filed on Jun. 13, 2018, which is a continuation-in-part of application No. 16/007,999, filed on Jun. 13, 2018, which is a continuation-in-part of application No. 15/488,712, filed on Apr. 17, 2017, now Pat. No. 10,039,710, which is a continuation-in-part of application No. 15/264,686, filed on Sep. 14, 2016, now abandoned.

(60) Provisional application No. 62/220,320, filed on Sep. 18, 2015.

(51) Int. Cl.

| A61K 31/137 | (2006.01) |
| A61K 9/00 | (2006.01) |
| A61K 47/02 | (2006.01) |
| A61P 37/08 | (2006.01) |
| A61K 47/18 | (2017.01) |
| A61K 47/10 | (2017.01) |

(52) U.S. Cl.
CPC .......... *A61K 31/137* (2013.01); *A61K 9/0043* (2013.01); *A61K 47/02* (2013.01); *A61K 47/10* (2013.01); *A61K 47/183* (2013.01); *A61K 47/186* (2013.01); *A61P 37/08* (2018.01)

(58) Field of Classification Search
CPC ..... A61K 31/137; A61K 47/40; A61K 9/0073
See application file for complete search history.

(56) References Cited

U.S. PATENT DOCUMENTS

2004/0076588 A1* 4/2004 Batycky ............... A61K 9/0075
424/46

* cited by examiner

*Primary Examiner* — San Ming R Hui
(74) *Attorney, Agent, or Firm* — Wood, Phillips, Katz, Clark & Mortimer

(57) ABSTRACT

The present invention is directed to epinephrine spray formulations. The present invention is further directed to methods of treating anaphylaxis by administering epinephrine spray formulations to subjects in need of such treatments.

4 Claims, 3 Drawing Sheets

EPINEPHRINE SPRAY FORMULATIONS

FIELD OF THE INVENTION

The present invention is directed to epinephrine spray formulations. The present invention is further directed to methods of treating anaphylaxis by administering epinephrine spray formulations to subjects in need of such treatments.

BACKGROUND OF THE INVENTION

Epinephrine (i.e. adrenaline) is a catecholamine with the following chemical structure:

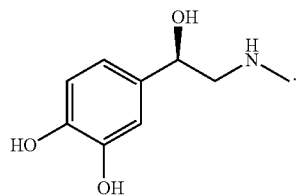

Epinephrine stimulates the alpha- and beta-adrenergic receptors of the sympathetic nervous system. Epinephrine binds to these adrenergic receptors leading to relief of many life-threatening symptoms of anaphylaxis including: relaxation of the smooth muscle in the bronchi of the lungs opening up the constricted airways; constriction of the blood vessels leading to decreased swelling of the tongue and throat and increased blood pressure; and finally, increased heart rate preventing or reversing cardiovascular collapse.

Epinephrine is commercially available as an injection (Adrenalin® a trademark of and available from Par Sterile Products, LLC) and an auto-injector (EpiPen® a trademark of and available from Mylan, Inc. and Auvi-Q® a trademark of and available from Sanofi Corporation). Epinephrine was previously available as a nasal spray (Adrenalin®) and an aerosol spray (Primatene® Mist trademark of Armstrong Pharmaceuticals, Inc.). Racepinephrine is commercially available as a 2.25% oral inhalation solution for use in nebulizers (S2® is available from Nephron Pharmaceuticals, Inc.). Epinephrine differs from racepinephrine in that epinephrine consists of only the L-isomer and racepinephrine is a 50/50 mixture of both the L- and D-isomers.

U.S. Pat. No. 8,628,805 is directed to a stable liquid adrenaline/bisulfite composition wherein the molar ratio of adrenaline to bisulfite is 1.31-2.20:1. U.S. Patent Application Publication No. 2012/0322884 A1 is directed to epinephrine nanoparticles, which can be incorporated into sublingual tablets. U.S. Patent Application Publication No. 2007/0202163 A1 is directed to epinephrine tablets for sublingual administration, which contain between 12% and 48% epinephrine. World Intellectual Property Organization ("W.I.P.O.") Publication No. 2014/127018 A1 is directed to a stable aqueous epinephrine formulation that requires cyclodextrin. W.I.P.O. Publication No. 2014/057365 A1 is directed to an injectable epinephrine formulation.

While there are various epinephrine formulations currently available, there remains a need in the art for a quick-onset spray formulation.

SUMMARY OF THE INVENTION

In one aspect, the present invention is directed to epinephrine spray formulations comprising:

from about 0.1% w/w to about 15% w/w epinephrine or a salt thereof, preferably the salt is selected from the group consisting of citrate, hydrochloride, halide, sulfate, phosphate, acetate, maleate, succinate, ascorbate, carbonate, mesylate and lactate;

from about 1% w/w to about 80% w/w water, preferably from about 5% to about 77% w/w, more preferably from about 10% to about 65% w/w or from about 15% to about 80% w/w; optionally, from about 1% w/w to about 99% w/w of a solvent selected from the group consisting of ethanol, glycerin, propylene glycol, polyethylene glycol 400 and a combination thereof; and optionally, from about 0.1% w/w to about 60% w/w of at least one acid, wherein the formulation has a pH from about 2 to about 7.0.

In one aspect, the present invention is directed to epinephrine spray formulations comprising:

from about 0.1% w/w to about 15% w/w epinephrine or a salt thereof, preferably the salt is selected from the group consisting of citrate, hydrochloride, halide, sulfate, phosphate, acetate, maleate, succinate, ascorbate, carbonate, mesylate and lactate;

from about 1% w/w to about 99% w/w of a solvent selected from the group consisting of water, ethanol, glycerin, propylene glycol, polyethylene glycol 400 and a combination thereof, preferably the solvent is a combination of water, ethanol and propylene glycol or water;

from about 0.1% w/w to about 60% w/w of at least one acid, preferably the at least one acid is diluted hydrochloric acid, wherein the formulation has a pH from about 2 to about 5.5.

In another aspect, the present invention is directed to epinephrine spray formulations, wherein the formulation is free of a propellant.

In another aspect, the present invention is directed to epinephrine spray formulations, wherein the formulation does not contain sorbitol.

In another aspect, the solvent of the present invention comprises from about 1% w/w to about 30% w/w glycerin.

In another aspect, the epinephrine spray formulations of the present invention further comprise a permeation enhancer comprising caprylic acid, preferably the caprylic acid is at a concentration from about 0.1% w/w to about 10% w/w, more preferably from about 0.1% w/w to about 5% w/w.

In another aspect, the permeation enhancer of the present invention further comprises a second compound selected from the group consisting of menthol, limonene, carvone, methyl chitosan, polysorbates, sodium lauryl sulfate, glyceryl oleate, caproic acid, enanthic acid, pelargonic acid, capric acid, undecylenic acid, lauric acid, myristic acid, palmitic acid, oleic acid, stearic acid, linolenic acid, arachidonic acid, benzethonium chloride, benzethonium bromide, benzalkonium chloride (BKC), cetylpyridium chloride, edetate disodium dihydrate (EDTA), sodium desoxycholate, sodium deoxyglycolate, sodium glycocholate, sodium caprate, sodium taurocholate, sodium hydroxybenzoyal amino caprylate, dodecyl dimethyl aminopropionate, L-lysine, glycerol oleate, glyceryl monostearate, citric acid, peppermint oil and a combination thereof, preferably menthol, preferably the menthol is at a concentration from about 0.1% to about 5% w/w, more preferably from about 0.1% to about 1% w/w.

In another aspect, the epinephrine spray formulations of the present invention contain no permeation enhancer.

In another aspect, the epinephrine spray formulations of the present invention further comprise an isotonicity agent comprising sodium chloride.

In another aspect, the epinephrine spray formulations of the present invention further comprise a stabilizer selected from the group consisting of butylated hydroxyanisole (BHA), butylated hydroxytoluene (BHT), ascorbic acid, methionine, sodium ascorbate, sodium thiosulfate, sodium bisulfite, sodium metabisulfite, ascorbyl palmitate, thioglycerol, alpha tocopherol (vitamin E), cysteine hydrochloride, benzalkonium chloride ("BKC"), citric acid, ethylenediaminetetraacetic acid (EDTA), sodium citrate, propyl gallate, 8-hydroxyquinoline, boric acid, histidine and combinations thereof, preferably the stabilizer comprises EDTA at a concentration from about 0.005% w/w to about 0.5% w/w, preferably the stabilizer comprises sodium bisulfite, sodium metabisulfite or a combination thereof at a concentration from about 0.005% w/w to about 5% w/w and preferably the stabilizer comprises BKC at a concentration from about 0.005% to about 0.5% w/w.

In another aspect, the epinephrine spray formulations of the present invention further comprise a preservative selected from the group consisting of butyl paraben, methyl paraben, ethyl paraben, propyl paraben, sodium benzoate, chlorobutanol, benzalkonium chloride (BKC), benzoic acid and combinations thereof, preferably BKC at a concentration from about 0.005% w/w to about 0.5% w/w.

In another aspect, the present invention is directed to epinephrine spray formulations comprising:
- from about 0.1% to about 15% w/w epinephrine, or a salt thereof;
- from about 1% to about 65% w/w hydrochloric acid with a normality from about 0.1 to 12N;
- from about 2% to about 60% w/w ethanol;
- from about 2% to about 98% w/w water;
- from about 1% to about 20% w/w propylene glycol;
- from about 0.001% to about 1% w/w sodium bisulfite;
- from about 0.001% to about 1% w/w sodium metabisulfite;
- from about 0.005% to about 1% w/w EDTA;
- optionally, a permeation enhancer selected from the group consisting of from about 0.5% to about 15% w/w caprylic acid, from about 0.1% to about 10% w/w menthol and a combination thereof; and
- optionally, benzalkonium chloride at a concentration from about 0.001% to about 0.1% w/w, wherein the formulation optionally has a pH from about 3 to about 7.0.

In another aspect, the present invention is directed to epinephrine spray formulations comprising:
- from about 0.1% to about 15% w/w epinephrine, or a salt thereof;
- from about 1% to about 65% w/w hydrochloric acid with a normality from about 0.1 to 12N;
- from about 2% to about 98% w/w water;
- from about 0.001% to about 7.5% w/w sodium bisulfite;
- from about 0.001% to about 7.5% w/w sodium metabisulfite;
- from about 0.005% to about 1% w/w EDTA;
- from about 0.1% to about 1% sodium chloride;
- optionally, benzalkonium chloride at a concentration from about 0.001% to about 0.1% w/w, wherein the formulation optionally has a pH from about 3 to about 5.5.

In another aspect, the present invention is directed to epinephrine spray formulations comprising:
- from about 0.1% to about 15% w/w epinephrine, or a salt thereof;
- from about 1% to about 65% w/w hydrochloric acid with a normality from about 0.1 to 12N;
- from about 2% to about 98% w/w water, preferably from about 10% to about 65% w/w;
- from about 0.005% to about 1% w/w sodium bisulfite;
- from about 0.005% to about 1% w/w EDTA;
- from about 0.005% to about 0.5% w/w BKC;
- optionally, from about 2% to about 60% w/w ethanol;
- optionally, from about 1% to about 20% w/w propylene glycol;
- optionally, from about 0.05% to about 5% w/w sodium chloride;
- optionally, benzalkonium chloride at a concentration from about 0.001% to about 0.1% w/w, wherein the formulation optionally has a pH from about 3 to about 7.0.

In another aspect, the present invention is directed to epinephrine spray formulations comprising:
- from about 0.1% w/w to about 15% w/w epinephrine or a salt thereof; and
- from about 1% to about 80% w/w water,
wherein administration to a human of 7 milligrams of epinephrine or a salt thereof in the formulation provides a pharmacokinetic parameter selected from the group consisting of a $C_{max}$ of at least about 1000 picograms per milliliter, a $T_{max}$ of 0.167 hours or less, an $AUC_{last}$ of at least 750 h*pg/mL, an $AUC_{inf}$ of at least 950 h*pg/mL and a combination thereof.

In another aspect, the present invention is directed to epinephrine spray formulations comprising:
- from about 0.1% w/w to about 15% w/w epinephrine or a salt thereof; and
- from about 1% to about 80% w/w water,
wherein administration to a human of 8.5 milligrams of epinephrine or a salt thereof in the formulation provides a pharmacokinetic parameter selected from the group consisting of a $C_{max}$ of at least about 1400 picograms per milliliter, a $T_{max}$ of 0.267 hours or less, an $AUC_{last}$ of at least 1200 h*pg/mL, an $AUC_{inf}$ of at least 1400 h*pg/mL and a combination thereof.

In another aspect, the present invention is directed to a method of treating anaphylaxis comprising administering to a subject in need thereof an epinephrine spray formulation of the present invention, preferably administration occurs via the intranasal route or sublingual route and wherein, optionally, the subject is suffering from seasonal allergies.

In another aspect, the present invention is directed to a method of treating anaphylaxis comprising administering to a subject in need thereof an epinephrine spray formulation of the present invention via unit dose or a multi-dose device that delivers more than one dose of the formulation, preferably via a bi-dose device that delivers two doses of the formulation.

In another aspect the present invention is directed to a method of treating anaphylaxis comprising administering via an assembled device an epinephrine formulation of the present invention.

DETAILED DESCRIPTION OF THE INVENTION

Definitions

Figure 1:
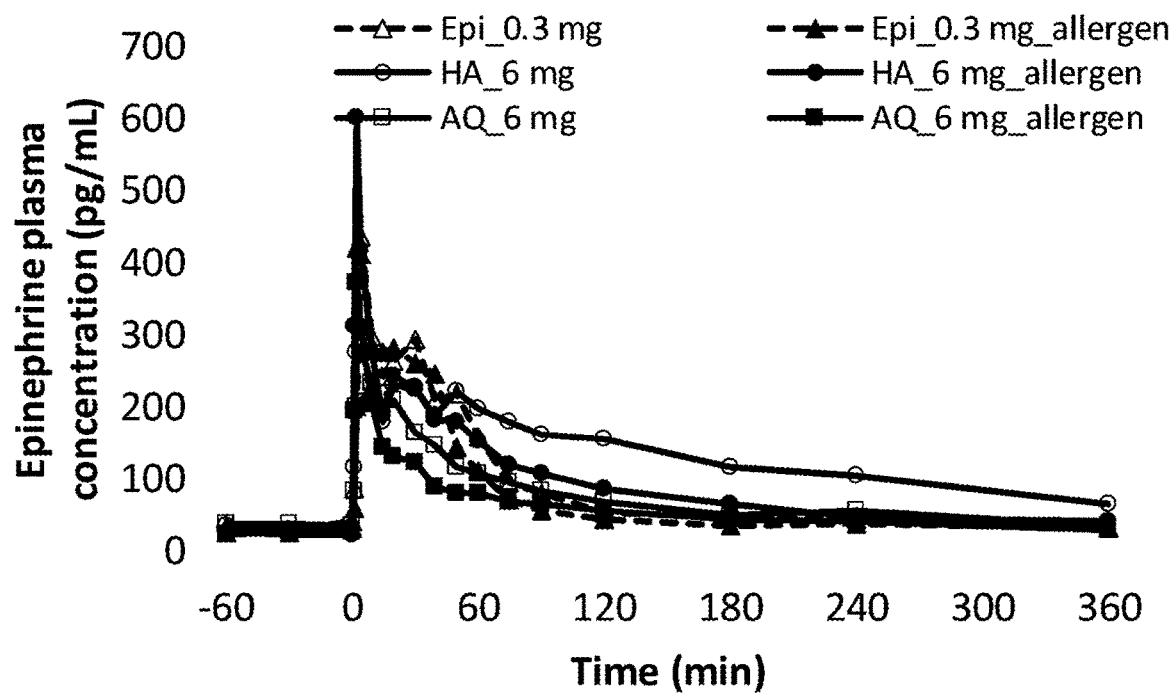
FIG. 1. Epinephrine plasma concentrations over first 6 hours post administration.

Applicants discovered epinephrine spray formulations that have improved bioavailability, a more rapid onset of action, and improved storage stability.

As used herein, "epinephrine" refers to the base.

As used herein, "free of propellant" refers to a formulation that is not administered using compressed gas.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

As used herein "% w/w" and "percent w/w" refer to the percent weight of the total formulation.

As used herein the term "effective amount" refers to the amount necessary to treat a patient in need thereof.

As used herein the term "treat", "treating" or "treatment" refers to ameliorating or inhibiting symptoms of type I allergies including anaphylaxis.

As used herein the term "subject" refers, but is not limited to, a person that is experiencing type I allergies including anaphylaxis.

As used herein the term "anaphylaxis" refers to an allergic reaction involving multiple organ systems in a subject upon contact with an allergen rather or not that allergen is identifiable.

As used herein the term "allergen" refers to any chemical capable of causing an immune system response in a subject including, but not limited to, chemicals found in drugs, food, plants, insect bites, and insect stings.

As used herein the term "seasonal allergies" refers to an allergic rhinitis. Seasonal allergies symptoms include, but are not limited to, itchy, watery eyes, sneezing, runny or stuffy nose, swollen nasal turbinates, itchy sinuses, throat or ear canals, ear congestion and postnasal drainage.

As used herein "nasal congestion" refers to a symptom of swollen nasal turbinates.

As used herein the term "pharmaceutically acceptable" refers to ingredients that are not biologically or otherwise undesirable for administration to a living subject.

"Sublingual" refers to administration of a substance via the mouth in such a way that the substance is rapidly absorbed via the blood vessels under the tongue.

"Intranasal" refers to administration of the composition to any portion of the nasal epithelium.

In one embodiment, the present invention is directed to epinephrine spray formulations comprising epinephrine, or a salt thereof.

Preferred epinephrine salts include citrate, hydrochloride, halide, sulfate, bitartrate, tartrate, phosphate, acetate, malate, maleate, succinate, ascorbate, carbonate, mesylate and lactate. One of skill in the art could use other pharmaceutically acceptable epinephrine salts in the formulations of the present invention. In a preferred embodiment, the formulations contain epinephrine or the pharmaceutically acceptable salt equivalent to from about 0.1% to about 15% w/w epinephrine. In a more preferred embodiment, the formulation contains epinephrine or the pharmaceutically acceptable salt equivalent to from about 0.1% to about 10% w/w of epinephrine. Other most preferred embodiments include formulations which contain epinephrine or the pharmaceutically acceptable salt equivalent to from about 0.1% w/w to about 10% w/w. In a most preferred embodiment, the epinephrine concentration between 3% and 10% w/w.

In another embodiment, the present invention is directed to epinephrine spray formulations comprising epinephrine, or a salt thereof, wherein the formulation is free of a propellant.

In another embodiment, the present invention is directed to epinephrine spray formulations comprising epinephrine, or a salt thereof, and one or more excipients selected from acids, solvents, stabilizers, permeation enhancers, viscosity modifiers, sweeteners, sweetness enhancers, pH modifiers, isotonicity agents and flavoring agents.

In a preferred embodiment, the formulations of the present invention contain from about 1% to about 65% w/w of an acid, more preferably from about 1% to about 45% w/w. Acids suitable for use in the present invention include, but are not limited to, hydrochloric acid, malic acid, tartaric acid, citric acid, succinic acid and combinations thereof. In a preferred embodiment, the acid is hydrochloric acid or malic acid, even more preferably from about 0.1N to about 12N hydrochloric acid, even more preferably from about 0.5 to about 6 N hydrochloric acid, even more preferably from about 0.5 N to about 3 N hydrochloric acid and most preferably 0.5 N or 3 N hydrochloric acid.

In a preferred embodiment, the formulations of the present invention contain from about 1% to 99% w/w of a solvent preferably from about 30% to about 99% w/w of the solvent.

Solvents suitable for use in the present invention include, but are not limited to, water, ethanol, glycerin, propylene glycol, polyethylene glycol 400 and combinations thereof, more preferably water.

In a preferred embodiment, the formulations of the present invention contain from about 0.001% to about 10% w/w of a stabilizer, preferably from about 0.005% to about 7.5% w/w, and even more preferably from about 0.01% to about 5% w/w. Stabilizers suitable for use in the present invention include, but are not limited to, butylated hydroxyanisole (BHA), butylated hydroxytoluene (BHT), ascorbic acid, methionine, sodium ascorbate, sodium thiosulfate, sodium bisulfite, sodium metabisulfite, ascorbyl palmitate, thioglycerol, alpha tocopherol (vitamin E), cysteine hydrochloride, citric acid, ethylenediaminetetraacetic acid ("EDTA"), sodium citrate, propyl gallate, 8-hydroxyquinoline, boric acid, histidine and combinations thereof. In a preferred embodiment, the stabilizer is selected from sodium metabisulfite, sodium bisulfite, disodium EDTA, 8-hydroxyquinoline and combinations thereof. In an even more preferred embodiment the stabilizer is a combination of sodium bisulfite, sodium metabisulfite, 8-Hydroxyquinoline and EDTA. In a further preferred embodiment, the formulations of the present invention contain from about 0.005% to 0.5% w/w EDTA as the stabilizer. In a more preferred embodiment, the formulations of the present invention contain from about 0.01% to 0.1% EDTA as the stabilizer. In a most preferred embodiment, the formulations of the present invention contain about 0.05% EDTA as the stabilizer. In a further preferred embodiment, the formulations of the present invention contain sodium bisulfite and sodium metabisulfite as the anti-oxidants at a concentration from about from about 0.005% to 5% w/w. In a more preferred embodiment, the formulations of the present invention contain sodium bisulfite or sodium metabisulfite or a combination thereof as the anti-oxidants at a concentration from about from about 0.05% to 1% w/w. In a more preferred embodiment, the formulations of the present invention contain sodium bisulfite or sodium metabisulfite combination thereof as the anti-oxidants at a concentration from about from about 0.05% to about 1% w/w, more preferably from about 0.1% to about 0.75% w/w. In a most preferred embodiment, the formulations of the present invention contain sodium bisulfite as the anti-oxidant at a concentration at about 0.15% or 0.3% or 0.5% or 0.75% w/w.

In some embodiments, the formulations of the present invention contain from about 0.001% w/w to about 15% w/w of a permeation enhancer, preferably from about 0.03% w/w to about 12% w/w, and even more preferably from about 0.05% to 10% w/w.

Permeation enhancers suitable for use in the present invention include, but are not limited to, caprylic acid, oleic acid, polysorbate 80, menthol, EDTA, disodium edetate, cetylpyridinium chloride, sodium lauryl sulfate, citric acid, sodium desoxycholate, sodium deoxyglycolate, glyceryl oleate, L-lysine and combinations thereof. Preferred permeation enhancers are caprylic acid, menthol or a combination thereof.

Viscosity modifiers suitable for the present invention include, but are not limited to, polyvinylpyrrolidone, carboxymethyl cellulose, hydroxypropylmethyl cellulose ("HPMC"), methyl cellulose, hydroxyethyl cellulose, glycerin, polyvinyl alcohol and combinations thereof. In a preferred embodiment, the viscosity modifier is HPMC.

Sweeteners suitable for the present invention include, but are not limited to, sucralose, sucrose, aspartame, saccharin, dextrose, mannitol, glycerin, xylitol and combinations thereof. In a preferred embodiment, the sweetener is sucralose.

In some embodiments, the formulations of the present invention contain from about 0.001% to about 1% of a sweetness enhancer. Sweetness enhancers suitable for the present invention include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

In a preferred embodiment, the formulations of the present invention are at a pH from about 2.0 to about 7.0. In a more preferred embodiment the formulations of the present invention are at a pH from about 3.0 to about 5.0. In a further preferred embodiment, the formulations of the present invention are at a pH from about 4.0 to about 5.0. In a most preferred embodiment the formulations of the present invention are at a pH of 4.5. pH modifiers suitable for the present invention include, but are not limited to, hydrochloric acid, citric acid, fumaric acid, lactic acid, sodium hydroxide, sodium citrate, sodium bicarbonate, sodium carbonate, ammonium carbonate and combinations thereof.

Preservatives suitable for the present invention include, but are not limited to, butyl paraben, methyl paraben, ethyl paraben, propyl paraben, sodium benzoate, chlorobutanol, benzalkonium chloride, benzoic acid and combinations thereof. In a preferred embodiment, the preservative is benzalkonium chloride. In a more preferred embodiment the benzalkonium chloride is at a concentration from about 0.01% to about 0.02% w/w, more preferably 0.01% or 0.02% w/w.

Flavoring agents suitable for the present invention include, but are not limited to, peppermint oil, menthol, spearmint oil, citrus oil, cinnamon oil, strawberry flavor, cherry flavor, raspberry flavor, orange oil and a combination thereof.

In preferred embodiment, the present invention is directed to epinephrine spray formulations comprising:
  from about 2.8% to about 4% w/w epinephrine, or a salt thereof;
  from about 32% to about 38% w/w hydrochloric acid with a normality from 0.5 to 3N;
  from about 10% to about 65% w/w ethanol;
  from about 2% to about 38% w/w water;
  about 5% w/w propylene glycol;
  from about 0.1% to about 0.75% w/w sodium bisulfite;
  about 0.05% w/w disodium EDTA;
  optionally, a permeation enhancer selected from the group consisting of from about 2% to about 10% w/w caprylic acid, from about 0.5% to about 1.0% w/w menthol and a combination thereof; and
  optionally, benzalkonium chloride at a concentration from about 0.01% to about 0.02% w/w, wherein the formulation optionally has a pH of about 4.5.

In another preferred embodiment, the present invention is directed to epinephrine spray formulations comprising:
  about 3.24% w/w epinephrine, or a salt thereof;
  about 36.2% w/w hydrochloric acid with a normality of 0.5;
  about 40% w/w ethanol;
  about 14.84% w/w water;
  about 5% w/w propylene glycol;
  about 0.01% w/w benzalkonium chloride; and
  from about 0.15% to about 0.3% w/w sodium bisulfite,
  wherein the formulation has a pH at about 4.5.

In another preferred embodiment, the present invention is directed to intranasal epinephrine spray formulations comprising:
  about 3.117% w/w epinephrine, or a salt thereof;
  about 34.8% w/w hydrochloric acid with a normality of 0.5;
  about 20% w/w ethanol;
  about 36.87% w/w water;
  about 5% w/w propylene glycol;
  about 0.01% w/w benzalkonium chloride;
  from about 0.15% w/w sodium bisulfite to about 0.3% w/w sodium bisulfite,
  wherein the formulation has a pH at about 4.5.

In another preferred embodiment, the present invention is directed to intranasal epinephrine spray formulations comprising:
  about 3.04% w/w epinephrine, or a salt thereof;
  about 33.8% w/w hydrochloric acid with a normality of 0.5;
  about 62.35% w/w water;
  about 0.01% w/w benzalkonium chloride;
  from about 0.15% w/w sodium bisulfite to about 0.3% w/w sodium bisulfite,
wherein the formulation has a pH at about 4.5.

An epinephrine spray formulation comprising:
  about 2.96% w/w epinephrine base;
  about 32.93% w/w hydrochloric acid with a normality of about 0.5N;
  about 0.05% w/w edetate disodium dihydrate;
  about 0.15% w/w sodium bisulfite;
  about 0.01% w/w benzalkonium chloride;
  about 0.6% w/w sodium chloride; and about 63.30% w/w water, wherein the formulation has a pH at about 4.5.

An epinephrine spray formulation comprising:
about 3.18% w/w epinephrine base;
about 35.47% w/w hydrochloric acid with a normality of about 0.5N;
about 0.05% w/w edetate disodium dihydrate;
about 0.15% w/w sodium bisulfite;
about 0.01% w/w benzalkonium chloride;
about 5% w/w propylene glycol;
about 40.0% w/w ethanol; and
about 16.14% w/w water, wherein the formulation has a pH at about 4.5.

An epinephrine spray formulation comprising:
about 5.923% w/w epinephrine base;
about 16.46% w/w hydrochloric acid with a normality of about 2N;
about 0.05% w/w edetate disodium dihydrate;
about 0.15% w/w sodium bisulfite;
about 0.01% w/w benzalkonium chloride;
about 0.6% w/w sodium chloride; and
about 76.81% w/w water, wherein the formulation has a pH at about 4.5.

An epinephrine spray formulation comprising:
about 5.923% w/w epinephrine base;
about 16.46% w/w hydrochloric acid with a normality of about 2N;
about 0.05% w/w edetate disodium dihydrate;
about 0.30% w/w sodium bisulfite;
about 0.01% w/w benzalkonium chloride;
about 0.6% w/w sodium chloride; and
about 76.66% w/w water, wherein the formulation has a pH at about 4.5.

An epinephrine spray formulation comprising:
about 6.356% w/w epinephrine base;
about 17.74% w/w hydrochloric acid with a normality of about 2N;
about 0.05% w/w edetate disodium dihydrate;
about 0.15% w/w sodium bisulfite;
about 0.01% w/w benzalkonium chloride;
about 40.0% w/w ethanol;
about 5% w/w propylene glycol
about 30.70% w/w water, wherein the formulation has a pH at about 4.5.

An epinephrine spray formulation comprising:
about 6.356% w/w epinephrine base;
about 17.74% w/w hydrochloric acid with a normality of about 2N;
about 0.05% w/w edetate disodium dihydrate;
about 0.30% w/w sodium bisulfite;
about 0.01% w/w benzalkonium chloride;
about 40.0% w/w ethanol;
about 5% w/w propylene glycol about 30.55% w/w water, wherein the formulation has a pH at about 4.5.

An epinephrine spray formulation comprising:
about 8.885% w/w epinephrine base;
about 24.70% w/w hydrochloric acid with a normality of about 2N;
about 0.05% w/w edetate disodium dihydrate;
about 0.15% w/w sodium bisulfite;
about 0.01% w/w benzalkonium chloride;
about 0.6% w/w sodium chloride; and
about 65.61% w/w water, wherein the formulation has a pH at about 4.5.

An epinephrine spray formulation comprising:
about 8.885% w/w epinephrine base;
about 24.70% w/w hydrochloric acid with a normality of about 2N;
about 0.05% w/w edetate disodium dihydrate;
about 0.45% w/w sodium bisulfite;
about 0.01% w/w benzalkonium chloride;
about 0.6% w/w sodium chloride; and
about 65.31% w/w water, wherein the formulation has a pH at about 4.5.

An epinephrine spray formulation comprising:
about 9.534% w/w epinephrine base;
about 26.60% w/w hydrochloric acid with a normality of about 2N;
about 0.05% w/w edetate disodium dihydrate;
about 0.15% w/w sodium bisulfite;
about 0.01% w/w benzalkonium chloride;
about 40.0% w/w ethanol;
about 5% w/w propylene glycol
about 18.65% w/w water, wherein the formulation has a pH at about 4.5.

An epinephrine spray formulation comprising:
about 9.534% w/w epinephrine base;
about 26.60% w/w hydrochloric acid with a normality of about 2N;
about 0.05% w/w edetate disodium dihydrate;
about 0.15% w/w sodium bisulfate;
about 0.01% w/w benzalkonium chloride;
about 40.0% w/w ethanol;
about 5% w/w propylene glycol
about 18.35% w/w water, wherein the formulation has a pH at about 4.5.

In another embodiment, administration to a human exposed to an allergen of 6 milligrams of epinephrine in the formulation #C1 of Table 62 below produced an epinephrine plasma concentration more than 100 picograms per milliliter at about 1-minute post administration.

In another embodiment, administration to a human not exposed to an allergen of 6 milligrams of epinephrine in the formulation #C1 of Table 62 below produced an epinephrine plasma concentration more than 100 picograms per milliliter at about 3-minutes post administration.

In another embodiment, administration to a human exposed to an allergen of 6 milligrams of epinephrine in the formulation #C2 of Table 62 below produced an epinephrine plasma concentration more than 100 picograms per milliliter at about 1-minute post administration.

In another embodiment, administration to a human exposed to an allergen of 6 milligrams of epinephrine in the formulation #C2 of Table 62 below produced an epinephrine plasma concentration more than 290 picograms per milliliter at about 1-minute post administration.

In another embodiment, administration to a human not exposed to an allergen of 6 milligrams of epinephrine in the formulation #C2 of Table 62 below produced an epinephrine plasma concentration more than 100 picograms per milliliter at about 3-minutes post administration.

In another aspect, the present invention is directed to epinephrine spray formulations comprising:
from about 0.1% w/w to about 15% w/w epinephrine or a salt thereof;
from about 2% to about 10% w/w propylene glycol;
from about 20% to about 50% w/w ethanol; and
from about 1% to about 80% w/w water,
wherein administration to a human of 7 milligrams of epinephrine or a salt thereof in the formulation provides:

a pharmacokinetic parameter selected from the group consisting of a $C_{max}$ (arithmetic mean) of at least about 1000 picograms per milliliter, a $T_{max}$ (arithmetic mean) of 0.167 hours or less, an $AUC_{last}$ (arithmetic mean) of at least 750 h*pg/mL, an $AUC_{inf}$ (arithmetic mean) of at least 950 h*pg/mL and a combination thereof; or a pharmacokinetic parameter selected from the group consisting of a $C_{max}$ (geometric mean) of at least about 500 picograms per milliliter, a $T_{max}$ of 0.167 hours or less, an $AUC_{last}$ (geometric mean) of at least about 500 h*pg/mL, an $AUC_{inf}$ (geometric mean) of at least about 800 h*pg/mL and a combination thereof;

a pharmacokinetic parameter selected from the group consisting of:

a $C_{max}$ (arithmetic mean) of about 1040 picograms per milliliter, a $T_{max}$ (arithmetic mean) of about 0.167 hours, an $AUC_{last}$ (arithmetic mean) of about 785 h*pg/mL, an $AUC_{inf}$ (arithmetic mean) of about 960 h*pg/mL and a combination thereof; or a pharmacokinetic parameter selected from the group consisting of a $C_{max}$ (geometric mean) of about 536 picograms per milliliter, an $AUC_{last}$ (geometric mean) of about 521 h*pg/mL, an $AUC_{inf}$ (geometric mean) of about 828 h*pg/mL and a combination thereof; or a plasma concentration of more than 70 picograms per milliliter in 1 minute or less following administration;

a plasma concentration of more than 750 picograms per milliliter in 3 minutes or less following administration;

provides a plasma concentration of more than 650 picograms per milliliter in 5 minutes or less following administration;

provides a plasma concentration of more than 600 picograms per milliliter in 7 minutes or less following administration; or provides a plasma concentration of more than 550 picograms per milliliter in 10 minutes or less following administration.

In another aspect, the present invention is directed to epinephrine spray formulations comprising:

from about 0.1% w/w to about 15% w/w epinephrine or a salt thereof; and from about 1% to about 80% w/w water, wherein administration to a human of 8.5 milligrams of epinephrine or a salt thereof in the formulation provides:

a pharmacokinetic parameter selected from the group consisting of a $C_{max}$ (arithmetic mean) of at least about 1400 picograms per milliliter, a $T_{max}$ of 0.267 hours or less, an $AUC_{last}$ (arithmetic mean) of at least 1200 h*pg/mL, an $AUC_{inf}$ (arithmetic mean) of at least 1400 h*pg/mL and a combination thereof;

a pharmacokinetic parameter selected from the group consisting of a $C_{max}$ (geometric mean) of at least about 650 picograms per milliliter, a $T_{max}$ of 0.267 hours or less, an $AUC_{last}$ (geometric mean) of at least about 800 h*pg/mL, an $AUC_{inf}$ (geometric mean) of at least about 10000 h*pg/mL and a combination thereof;

a pharmacokinetic parameter selected from the group consisting of a $C_{max}$ (arithmetic mean) of about 1420 picograms per milliliter, a median $T_{max}$ of about 0.267 hours, an $AUC_{last}$ (arithmetic mean) of about 1200 h*pg/mL, an $AUC_{last}$ (arithmetic mean) of about 1440 h*pg/mL and a combination thereof;

a pharmacokinetic parameter selected from the group consisting of a $C_{max}$ (geometric mean) of about 686 picograms per milliliter, an $AUC_{last}$ (geometric mean) of about 813 h*pg/mL, an $AUC_{inf}$ (geometric mean) of about 10308 h*pg/mL and a combination thereof;

a plasma concentration of more than 200 picograms per milliliter in 1 minute or less following administration;

a plasma concentration of more than 850 picograms per milliliter in 3 minutes or less following administration;

a plasma concentration of more than 1000 picograms per milliliter in 5 minutes or less following administration;

a plasma concentration of more than 975 picograms per milliliter in 7 minutes or less following administration; or a plasma concentration of more than 950 picograms per milliliter in 10 minutes or less following administration.

In another aspect, the present invention is directed to epinephrine spray formulations comprising:

from about 0.1% w/w to about 15% w/w epinephrine or a salt thereof;

from about 2% to about 10% w/w propylene glycol;

from about 20% to about 50% w/w ethanol; and from about 1% to about 80% w/w water, wherein administration to a human of 7 milligrams of epinephrine or a salt thereof in the formulation provides:

a geometric mean plasma concentration at 1 minute post-administration of 4.3 times compared to a geometric mean plasma concentration following administration of 0.3 milligrams of epinephrine in a second formulation;

a geometric mean plasma concentration at 3 minutes post-administration of 1.7 times compared to a geometric mean plasma concentration following administration of 0.3 milligrams of epinephrine in a second formulation;

a geometric mean plasma concentration at 5 minutes post-administration of 1.3 times compared to a geometric mean plasma concentration following administration of 0.3 milligrams of epinephrine in a second formulation;

a geometric mean plasma concentration at 7 minutes post-administration of 1.5 times compared to a geometric mean plasma concentration following administration of 0.3 milligrams of epinephrine in a second formulation;

a geometric mean plasma concentration at 10 minutes post-administration of 1.6 times compared to a geometric mean plasma concentration following administration of 0.3 milligrams of epinephrine in a second formulation;

a geometric mean plasma concentration at 15 minutes post-administration of 1.8 times compared to a geometric mean plasma concentration following administration of 0.3 milligrams of epinephrine in a second formulation;

a geometric mean plasma concentration at 20 minutes post-administration of 1.4 times compared to a geometric mean plasma concentration following administration of 0.3 milligrams of epinephrine in a second formulation;

a geometric mean plasma concentration at 30 minutes post-administration of 1.4 times compared to a geometric mean plasma concentration following administration of 0.3 milligrams of epinephrine in a second formulation;

a geometric mean plasma concentration at 45 minutes post-administration of 1.7 times compared to a geometric mean plasma concentration following administration of 0.3 milligrams of epinephrine in a second formulation; or a geometric mean plasma concentration at 60 minutes post-administration of 2.4 times compared to a geometric mean plasma concentration following administration of 0.3 milligrams of epinephrine in a second formulation, wherein in the second formulation consists of 0.3 milligrams epinephrine, 1.8 milligrams sodium chloride, 0.5 milligrams sodium metabisulfite, hydrochloric acid to adjust pH, and water for injection.

In another aspect, the present invention is directed to epinephrine spray formulations comprising:

from about 0.1% w/w to about 15% w/w epinephrine or a salt thereof;
from about 2% to about 10% w/w propylene glycol;
from about 20% to about 50% w/w ethanol; and
from about 1% to about 80% w/w water,
wherein administration to a human of 8.5 milligrams of epinephrine or a salt thereof in the formulation provides:
a geometric mean plasma concentration at 1 minute post-administration of 5.3 times compared to a geometric mean plasma concentration following administration of 0.3 milligrams of epinephrine in a second formulation;
a geometric mean plasma concentration at 3 minutes post-administration of 1.9 times compared to a geometric mean plasma concentration following administration of 0.3 milligrams of epinephrine in a second formulation;
a geometric mean plasma concentration at 5 minutes post-administration of 2.0 times compared to a geometric mean plasma concentration following administration of 0.3 milligrams of epinephrine in a second formulation;
a geometric mean plasma concentration at 7 minutes post-administration of 2.4 times compared to a geometric mean plasma concentration following administration of 0.3 milligrams of epinephrine in a second formulation;
a geometric mean plasma concentration at 10 minutes post-administration of 2.8 times compared to a geometric mean plasma concentration following administration of 0.3 milligrams of epinephrine in a second formulation;
a geometric mean plasma concentration at 15 minutes post-administration of 2.8 times compared to a geometric mean plasma concentration following administration of 0.3 milligrams of epinephrine in a second formulation;
a geometric mean plasma concentration at 20 minutes post-administration of 2.4 times compared to a geometric mean plasma concentration following administration of 0.3 milligrams of epinephrine in a second formulation;
a geometric mean plasma concentration at 30 minutes post-administration of 2.0 times compared to a geometric mean plasma concentration following administration of 0.3 milligrams of epinephrine in a second formulation;
a geometric mean plasma concentration at 45 minutes post-administration of 2.7 times compared to a geometric mean plasma concentration following administration of 0.3 milligrams of epinephrine in a second formulation; or
a geometric mean plasma concentration at 60 minutes post-administration of 3.4 times compared to a geometric mean plasma concentration following administration of 0.3 milligrams of epinephrine in a second formulation,
wherein in the second formulation consists of 0.3 milligrams epinephrine, 1.8 milligrams sodium chloride, 0.5 milligrams sodium metabisulfite, hydrochloric acid to adjust pH, and water for injection.

In another aspect, the present invention is directed to epinephrine spray formulations comprising:
from about 0.1% w/w to about 15% w/w epinephrine or a salt thereof;
from about 2% to about 10% w/w propylene glycol;
from about 20% to about 50% w/w ethanol; and
from about 1% to about 80% w/w water,
wherein administration to a human of 7 milligrams of epinephrine or a salt thereof in the formulation provides:
a geometric mean $AUC_{0-0.017}$ of 4.2 times compared to a geometric mean $AUC_{0-0.017}$ following administration of 0.3 milligrams of epinephrine in a second formulation;
a geometric mean $AUC_{0-0.05}$ of 2 times compared to a geometric mean $AUC_{0-0.5}$ following administration of 0.3 milligrams of epinephrine in a second formulation;
a geometric mean $AUC_{0-0.083}$ of 1.7 times compared to a geometric mean $AUC_{0-0.083}$ following administration of 0.3 milligrams of epinephrine in a second formulation;
a geometric mean $AUC_{0-0.117}$ of 1.6 times compared to a geometric mean $AUC_{0-0.117}$ following administration of 0.3 milligrams of epinephrine in a second formulation;
a geometric mean $AUC_{0-0.167}$ of 1.6 times compared to a geometric mean $AUC_{0-0.167}$ following administration of 0.3 milligrams of epinephrine in a second formulation;
a geometric mean $AUC_{0-0.25}$ of 1.6 times compared to a geometric mean $AUC_{0-0.25}$ following administration of 0.3 milligrams of epinephrine in a second formulation;
a geometric mean $AUC_{0-0.33}$ of 1.6 times compared to a geometric mean $AUC_{0-0.33}$ following administration of 0.3 milligrams of epinephrine in a second formulation;
a geometric mean $AUC_{0-0.5}$ of 1.5 times compared to a geometric mean $AUC_{0-0.5}$ following administration of 0.3 milligrams of epinephrine in a second formulation;
a geometric mean $AUC_{0-0.75}$ of 1.5 times compared to a geometric mean $AUC_{0-0.75}$ following administration of 0.3 milligrams of epinephrine in a second formulation; or
a geometric mean $AUC_{0-1}$ of 1.6 times compared to a geometric mean $AUC_{0-1}$ following administration of 0.3 milligrams of epinephrine in a second formulation.

In another aspect, the present invention is directed to epinephrine spray formulations comprising:
from about 0.1% w/w to about 15% w/w epinephrine or a salt thereof;
from about 2% to about 10% w/w propylene glycol;
from about 20% to about 50% w/w ethanol; and
from about 1% to about 80% w/w water,
wherein administration to a human of 8.5 milligrams of epinephrine or a salt thereof in the formulation provides:
a geometric mean $AUC_{0-0.017}$ of 5 times compared to a geometric mean $AUC_{0-0.017}$ following administration of 0.3 milligrams of epinephrine in a second formulation;
a geometric mean $AUC_{0-0.05}$ of 2.3 times compared to a geometric mean $AUC_{0-0.5}$ following administration of 0.3 milligrams of epinephrine in a second formulation;
a geometric mean $AUC_{0-0.083}$ of 2.1 times compared to a geometric mean $AUC_{0-0.083}$ following administration of 0.3 milligrams of epinephrine in a second formulation;
a geometric mean $AUC_{0-0.117}$ of 2.1 times compared to a geometric mean $AUC_{0-0.117}$ following administration of 0.3 milligrams of epinephrine in a second formulation;
a geometric mean $AUC_{0-0.167}$ of 2.3 times compared to a geometric mean $AUC_{0-0.167}$ following administration of 0.3 milligrams of epinephrine in a second formulation;
a geometric mean $AUC_{0-0.25}$ of 2.5 times compared to a geometric mean $AUC_{0-0.25}$ following administration of 0.3 milligrams of epinephrine in a second formulation;
a geometric mean $AUC_{0-0.33}$ of 2.5 times compared to a geometric mean $AUC_{0-0.33}$ following administration of 0.3 milligrams of epinephrine in a second formulation;
a geometric mean $AUC_{0-0.5}$ of 2.4 times compared to a geometric mean $AUC_{0-0.5}$ following administration of 0.3 milligrams of epinephrine in a second formulation;
a geometric mean $AUC_{0-0.75}$ of 2.4 times compared to a geometric mean $AUC_{0-0.75}$ following administration of 0.3 milligrams of epinephrine in a second formulation; or
a geometric mean $AUC_{0-1}$ of 2.5 times compared to a geometric mean $AUC_{0-1}$ following administration of 0.3 milligrams of epinephrine in a second formulation.

In another aspect, the present invention is directed to epinephrine spray formulations comprising:

from about 3% to about 6% w/w epinephrine base;
from about 20% to about 30% w/w hydrochloric acid with a normality of about 1.0N;
from about 0.025% to about 0.075% w/w edetate disodium dihydrate;
from about 0.15% to about 0.30% w/w sodium bisulfate;
from about 0.005% to about 0.02% w/w benzalkonium chloride;
from about 35% to about 45% w/w ethanol;
from about 2.5% to about 7.5% w/w propylene glycol; and
from about 20% to about 30% w/w water.

In another aspect, the present invention is directed to epinephrine spray formulations comprising:
from about 3% to about 5% w/w epinephrine base;
from about 20% to about 25% w/w hydrochloric acid with a normality of about 1.0N;
from about 0.025% to about 0.075% w/w edetate disodium dihydrate;
from about 0.15% to about 0.25% w/w sodium bisulfate;
from about 0.005% to about 0.02% w/w benzalkonium chloride;
from about 35% to about 45% w/w ethanol;
from about 2.5% to about 7.5% w/w propylene glycol; and
from about 20% to about 40% w/w water.

In another aspect, the present invention is directed to epinephrine spray formulations comprising:
from about 0.1% w/w to about 15% w/w epinephrine or a salt thereof;
from about 2% to about 10% w/w propylene glycol;
from about 20% to about 50% w/w ethanol; and
from about 1% to about 80% w/w water,
wherein administration to a human of 7 milligrams of epinephrine or a salt thereof in the formulation provides:
a geometric mean $C_{max}$ of about 86.2% compared to a geometric mean $C_{max}$ following intramuscular administration of 0.3 milligrams of epinephrine in a second formulation; $AUC_{last}$ of about 154% compared to a geometric mean $AUC_{last}$ following administration of 0.3 milligrams of epinephrine in a second formulation;
$AUC_{inf}$ of about 217% compared to a geometric mean $AUC_{inf}$ following administration of 0.3 milligrams of epinephrine in a second formulation;
a geometric mean $C_{max}$ of about 101% compared to a geometric mean $C_{max}$ following intramuscular administration of 0.5 milligrams of epinephrine in a third formulation;
$AUC_{last}$ of about 94.5% compared to a geometric mean $AUC_{last}$ following administration of 0.5 milligrams of epinephrine in a third formulation; or
$AUC_{inf}$ of about 120% compared to a geometric mean $AUC_{inf}$ following administration of 0.5 milligrams of epinephrine in a third formulation,
wherein the second formulation consists of 0.3 milligrams epinephrine, 1.8 milligrams sodium chloride, 0.5 milligrams sodium metabisulfite, hydrochloric acid to adjust pH, and water for injection and wherein the third formulation consists of 1.0 milligrams epinephrine, 6.15 milligrams sodium chloride, 0.457 milligrams sodium metabisulfite, 0.920 milligrams sodium hydroxide, 2.25 milligrams tartaric acid, 0.20 milligrams disodium edetate dihydrate, hydrochloric acid to adjust pH, milligrams chlorobutanol and water for injection.

In another aspect, the present invention is directed to epinephrine spray formulations comprising:
a geometric mean $C_{max}$ of about 111% compared to a geometric mean $C_{max}$ following administration of 0.3 milligrams of epinephrine in a second formulation;
$AUC_{last}$ of about 241% compared to a geometric mean $AUC_{last}$ following administration of 0.3 milligrams of epinephrine in a second formulation;
$AUC_{inf}$ of about 282% compared to a geometric mean $AUC_{inf}$ following administration of 0.3 milligrams of epinephrine in a second formulation;
a geometric mean $C_{max}$ of about 130% compared to a geometric mean $C_{max}$ following intramuscular administration of 0.5 milligrams of epinephrine in a third formulation;
$AUC_{last}$ of about 147% compared to a geometric mean $AUC_{last}$ following administration of 0.5 milligrams of epinephrine in a third formulation; or
$AUC_{inf}$ of about 155% compared to a geometric mean $AUC_{inf}$ following administration of 0.5 milligrams of epinephrine in a third formulation,
wherein the second formulation consists of 0.3 milligrams epinephrine, 1.8 milligrams sodium chloride, 0.5 milligrams sodium metabisulfite, hydrochloric acid to adjust pH, and water for injection and wherein the third formulation consists of 1.0 milligrams epinephrine, 6.15 milligrams sodium chloride, 0.457 milligrams sodium metabisulfite, 0.920 milligrams sodium hydroxide, 2.25 milligrams tartaric acid, 0.20 milligrams disodium edetate dihydrate, hydrochloric acid to adjust pH, milligrams chlorobutanol and water for injection.

In another embodiment, the formulations of the present invention are capable of producing a droplet size distribution at 3 cm wherein the mean DV (10) is from about 15 to about 18 microns during administration.

In another embodiment, the formulations of the present invention are capable of producing a droplet size distribution at 3 cm wherein the mean DV (50) is from about 30 to about 34 microns during administration.

In another embodiment, the formulations of the present invention are capable of producing a droplet size distribution at 3 cm wherein the mean DV (90) is from about 120 to about 230 microns during administration.

In another embodiment, the formulations of the present invention are capable of producing a spray span ((Dv90−Dv10)/Dv50) at 3 cm of from about 3 to about 7.

In another embodiment, the formulations of the present invention are capable of producing a droplet size distribution at 6 cm wherein the mean DV (10) is from about 22 to about 25 microns during administration.

In another embodiment, the formulations of the present invention are capable of producing a droplet size distribution at 6 cm wherein the mean DV (50) is from about 36 to about 41 microns during administration.

In another embodiment, the formulations of the present invention are capable of producing a droplet size distribution at 6 cm wherein the mean DV (90) is from about 59 to about 231 microns during administration.

In another embodiment, the formulations of the present invention are capable of producing a spray span ((Dv90−Dv10)/Dv50) at 6 cm of from about 1 to about 6.

In another embodiment, the formulations of the present invention are capable of producing a spray pattern at 3 cm wherein the Dmin is from about 18 to about 23 millimeters during administration.

In another embodiment, the formulations of the present invention are capable of producing a spray pattern at 3 cm wherein the Dmax is from about 29 to about 33 millimeters during administration.

In another embodiment, the formulations of the present invention are capable of producing a spray pattern at 3 cm wherein the ovality ratio is from about 1.4 to about 1.7 during administration.

In another embodiment, the formulations of the present invention are capable of producing a spray pattern at 6 cm wherein the Dmin is from about 26 to about 33 millimeters during administration.

In another embodiment, the formulations of the present invention are capable of producing a spray pattern at 6 cm wherein the Dmax is from about 47 to about 52 millimeters during administration.

In another embodiment, the formulations of the present invention are capable of producing a spray pattern at 6 cm wherein the ovality ratio is from about 1.6 to about 1.9 during administration.

In another embodiment, the formulations of the present invention are capable of producing a plume geometry at 3 cm wherein the angle is from about 49° to about 64°.

In another embodiment, the formulations of the present invention are capable of producing a plume geometry at 3 cm wherein the width is from about 27 to about 38 millimeters.

In another embodiment, the formulations of the present invention are capable of producing a plume geometry at 3 cm wherein the angle is from about 37° to about 44°.

In another embodiment, the formulations of the present invention are capable of producing a plume geometry at 3 cm wherein the width is from about 37 to about 44 millimeters.

In one embodiment, the present invention is directed to a method of treating anaphylaxis comprising administering via an assembled device an epinephrine formulation comprising from about 0.1% w/w to about 15% w/w epinephrine or a salt thereof and from about 1% to about 80% w/w water, wherein the formulation has a pH from about 2 to about 7.0.

In a preferred embodiment, the assembled device comprises a reservoir, a plunger, a cannula, a spray pin, a reservoir holder and an actuator or a reservoir, a piston and a swirl chamber.

In another preferred embodiment, the assembled device delivers one or more doses of the epinephrine formulation.

In another preferred embodiment, the assembled device is a unit-dose device that delivers one dose of the epinephrine formulation upon a single actuation and comprises a single reservoir containing not more than 250 μL of the epinephrine formulation, preferably about 237 or not more than 140 preferably about 127 μL.

In another preferred embodiment, the assembled device is a unit-dose device that delivers about 200 μL or about 100 μL of the pharmaceutical formulation upon a single actuation.

In another preferred embodiment, the assembled device is a bi-dose device that delivers two doses of the epinephrine formulation upon two actuations and delivers about 100 μL of the epinephrine formulation per actuation.

In another preferred embodiment, the assembled device is a multi-dose device that delivers multiple doses of the epinephrine formulation upon multiple actuations and delivers about 100 μL of the pharmaceutical solution per actuation.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1

An epinephrine spray was prepared as follows using the components and amounts listed in Table 1 below. All of the solvents were purged with nitrogen prior to use. Excipients including 0.5 N hydrochloric acid ("HCl"), malic acid, ethanol and propylene glycol, EDTA, sodium chloride, sodium bisulfate, sodium metabisulfite, and 8-hydroxyquinoline were dissolved in water while stirring at room temperature. Epinephrine base was then added to the excipient solution. Finally, sodium hydroxide ("NaOH")/hydrochloric acid (HCl)) was used to adjust final pH.

TABLE 1

| Epinephrine Formulations | | | | | | | | | | | |
|---|---|---|---|---|---|---|---|---|---|---|---|
| % w/w | #1 | #2 | #3 | #4 | #5 | #6 | #7 | #8 | #9 | #10 | #11 |
| Epinephrine base | 1.0 | 1.0 | 1.0 | 1.0 | 1.0 | 7.5 | 1 | 3.0 | 3.0 | 3.0 | 3.0 |
| HCl (0.5N) | 10.66 | 10.66 | 10.66 | 10.66 | 10.66 | — | 11.35 | — | 32.6 | 32.6 | 32.6 |
| EDTA | 0.05 | 0.05 | 0.05 | 0.05 | 0.05 | — | — | — | 0.05 | 0.05 | 0.05 |
| Sodium metabisulfite | 0.01 | 0.015 | 0.02 | 0.025 | 0.025 | 0.25 | 0.025 | 0.04 | — | — | — |
| sodium bisulfite | 0.01 | 0.015 | 0.02 | 0.025 | 0.025 | — | 0.025 | | 0.05 | 0.2 | 0.2 |
| Propylene Glycol | — | — | — | — | — | — | — | — | — | — | 5 |
| Menthol | — | — | — | — | — | — | — | — | — | — | 5 |
| Chlorobutanol | — | — | — | — | — | — | — | — | — | 0.5 | — |
| Sucralose | — | — | — | — | — | — | — | — | — | 0.5 | 0.5 |
| 8-Hydroxyquinoline | — | — | — | — | 0.02 | — | — | — | — | — | — |
| Ethanol | — | — | — | — | — | 15 | — | — | — | — | 50 |
| Malic Acid | — | — | — | — | — | 2.0 | — | 1.65 | — | — | — |
| Water | 88.27 | 88.26 | 88.25 | 88.24 | 88.22 | 79.75 | 87.6 | 95.31 | 64.3 | 63.15 | 4.15 |
| pH adjusted with NaOH | 100 pH 4.5 | 100 pH 4.5 | 100 pH 4.5 | 100 pH 4.5 | 100 pH 4.5 | 100 pH 4.5 | 100 pH 4.5 | 100 pH 4.5 | 100 pH 4.5 | 100 pH 4.5 | 100 pH 4.5 |

Example 2

The formulations listed in Table 1 were subjected to stability at 40° C.±2° C./75%±5% relative humidity and 25° C.±2° C./60%±5% relative humidity. The stability of the formulations was analyzed at specified time points by evaluating their potency (assay value) and impurity levels. Assay and impurities were detected using high-performance liquid chromatography with an ultraviolet detector. The assay was performed at 280 nm and indicated as a % of initial concentration. For all impurities, analysis was performed at 210 nm and 280 nm and expressed as a % area. Amounts of particular impurities are listed in Tables 2 to 20 as a percentage of area of each formulation along with amount of total impurities. Relative retention time ("RRT") is given for each impurity. "ND" indicates that the impurity was not detected. "BQL" indicates purity is below quantification limit.

TABLE 2

Stability Data for Epinephrine Spray Formulation #1 stored at 40° C. ± 2° C./75% ± 5% Relative Humidity

| 40° C. Formulation #1 | RRT | 0 Week | 2 Weeks | 4 Weeks |
|---|---|---|---|---|
| Appearance | | Clear | Clear | Clear |
| Assay (% of initial conc.) | | 100.00 | 97.94 | 95.80 |
| % Racemization | | 0.60 | 0.93 | 1.54 |
| pH | | 4.50 | 3.52 | 3.29 |
| % Impurity F | 0.19 | 0.13 | 1.07 | 1.51 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | ND | 0.10 | 0.15 |
| | 0.23 | ND | ND | 0.02 |
| | 3.11 | ND | BQL | 0.03 |
| | 3.26 | ND | BQL | 0.02 |
| % Total Impurities | | 0.20 | 1.24 | 1.80 |

TABLE 3

Stability Data for Epinephrine Spray Formulation #2 stored at 40° C. ± 2° C./75% ± 5% Relative Humidity

| 40° C. Formulation #2 | RRT | 0 Week | 2 Weeks | 4 Weeks |
|---|---|---|---|---|
| Appearance | | Clear | Clear | Clear |
| Assay (% of initial conc.) | | 100.00 | 96.02 | 97.32 |
| % Racemization | | 0.60 | 0.91 | 1.77 |
| pH | | 4.50 | 3.39 | 3.14 |
| % Impurity F | 0.19 | 0.14 | 1.27 | 1.91 |
| % Synephrine | 1.26 | ND | ND | ND |
| % Epinephrone | 1.38 | ND | ND | BQL |
| % Methoxy | 1.88 | 0.07 | 0.07 | 0.07 |
| % Unknown Impurity | 0.21 | ND | 0.10 | 0.11 |
| | 0.23 | ND | ND | BQL |
| | 3.26 | ND | ND | ND |
| % Total Impurities | | 0.21 | 1.44 | 2.09 |

TABLE 4

Stability Data for Epinephrine Spray Formulation #3 stored at 40° C. ± 2° C./75% ± 5% Relative Humidity

| 40° C. Formulation #3 | RRT | 0 Week | 2 Weeks | 4 Weeks | 8 Weeks | 3 Months |
|---|---|---|---|---|---|---|
| Appearance | | Clear | Clear | Clear | Clear | Clear |
| Assay (% of initial conc.) | | 100.00 | 98.22 | 96.87 | 94.56 | 93.27 |
| % Racemization | | 0.60 | 1.01 | 1.48 | 3.67 | 4.23 |
| pH | | 4.50 | 3.37 | 3.14 | 3.01 | — |
| % Impurity F | 0.19 | 0.13 | 1.27 | 2.19 | 3.05 | 3.18 |
| % Synephrine | 1.26 | ND | ND | ND | ND | ND |
| % Epinephrone | 1.36 | ND | ND | BQL | BQL | BQL |
| % Methoxy | 1.88 | 0.07 | 0.07 | 0.07 | 0.07 | 0.07 |
| % Unknown Impurity | 0.21 | ND | 0.08 | 0.07 | 0.08 | 0.24 |
| | 3.11 | ND | ND | BQL | BQL | BQL |
| | 3.26 | ND | ND | BQL | BQL | BQL |
| % Total Impurities | | 0.20 | 1.42 | 2.33 | 3.20 | 3.49 |

TABLE 5

Stability Data for Epinephrine Spray Formulation #4 stored at 40° C. ± 2° C./75% ± 5% Relative Humidity

| 40° C. Formulation #4 | RRT | 0 Week | 1 Week | 2 Weeks | 4 Weeks | 6 Weeks | 8 Weeks | 3 Months | 4 Months |
|---|---|---|---|---|---|---|---|---|---|
| Appearance | | Clear | Clear | Clear | Clear | Clear | Clear | Clear | Clear |
| Assay (% of initial conc.) | | 100.0 | 100.7 | 98.54 | 98.35 | 96.02 | 94.44 | 92.60 | 89.34 |
| % Racemization | | 0.60 | 0.68 | — | — | 3.41 | 3.46 | 5.75 | 9.20 |
| % Impurity F | 0.19 | 0.15 | 0.78 | 1.29 | 2.33 | 3.16 | 3.83 | 4.36 | 4.65 |
| % Synephrine | 1.26 | ND | ND | ND | ND | ND | ND | ND | ND |
| % Epinephrone | 1.36 | ND | ND | ND | BQL | BQL | BQL | BQL | BQL |
| % Methoxy | 1.88 | 0.08 | 0.08 | 0.08 | 0.08 | 0.08 | 0.08 | 0.08 | 0.09 |
| % Unknown Impurity | 0.21 | ND | ND | 0.05 | 0.08 | 0.07 | 0.09 | 0.22 | 0.23 |
| | 3.11 | ND | ND | ND | BQL | BQL | BQL | BQL | 0.05 |
| | 3.26 | ND | ND | ND | BQL | BQL | BQL | BQL | BQL |
| % Total Impurities | | 0.23 | 0.86 | 1.42 | 2.49 | 3.31 | 4.00 | 4.66 | 5.02 |

TABLE 6

Stability Data for Epinephrine Spray Formulation #5 stored at 40° C. ± 2° C./75% ± 5% Relative Humidity

| 40° C. Formulation #5 | RRT | 0 Week | 2 Weeks | 4 Weeks | 8 Weeks | 3 Months |
|---|---|---|---|---|---|---|
| Appearance | | Clear | Clear | Clear | Clear | Clear |
| Assay (% of initial conc.) | | 100.00 | 98.36 | 96.88 | 95.35 | 93.34 |
| % Racemization | | 0.60 | 0.85 | 1.08 | 2.63 | 4.23 |
| pH | | 4.50 | 3.64 | 3.37 | 3.20 | — |
| % Impurity F | 0.19 | 0.15 | 1.48 | 2.50 | 3.50 | 3.75 |
| % Synephrine | 1.26 | ND | ND | ND | ND | ND |
| % Epinephrone | 1.36 | ND | ND | BQL | BQL | BQL |
| % Methoxy | 1.88 | 0.07 | 0.07 | 0.07 | 0.07 | 0.07 |
| % Unknown Impurity | 0.21 | ND | 0.10 | 0.11 | 0.15 | 0.35 |
| | 0.88 | ND | ND | ND | ND | BQL |
| | 3.11 | ND | ND | BQL | BQL | BQL |
| | 3.26 | ND | ND | BQL | BQL | BQL |
| % Total Impurities | | 0.22 | 1.65 | 2.68 | 3.72 | 4.17 |

TABLE 7

Stability Data for Epinephrine Spray Formulation #6 stored at 40° C. ± 2° C./75% ± 5% Relative Humidity

| 40° C. Formulation #6 | RRT | 0 Week | 2 Weeks | 1 Month |
|---|---|---|---|---|
| Appearance | | Clear | Clear | Clear |
| Assay (% of initial conc.) | | 100.00 | 97.75 | 95.95 |
| % Impurity F | 0.19 | 0.15 | 2.38 | 4.04 |
| % Synephrine | 1.26 | ND | ND | ND |
| % Epinephrone | 1.36 | ND | BQL | BQL |
| % Methoxy | 1.88 | BQL | BQL | BQL |
| % Unknown Impurity | 0.21 | ND | 0.05 | 0.08 |
| % Total Impurities | | 0.15 | 2.43 | 4.08 |

TABLE 8

Stability Data for Epinephrine Spray Formulation #7 stored at 40° C. ± 2° C./75% ± 5% Relative Humidity

| 40° C. Formulation #7 | RRT | 0 Week | 2 Weeks | 4 Weeks |
|---|---|---|---|---|
| Appearance | | Clear | Clear | Clear |
| % Impurity F | 0.19 | 0.32 | 1.85 | 2.75 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | 0.17 | 0.36 | 0.44 |
| % Total Impurities | | 0.56 | 2.28 | 3.26 |

TABLE 9

Stability Data for Epinephrine Spray Formulation #8 stored at 40° C. ± 2° C./75% ± 5% Relative Humidity

| 40° C. Formulation #8 | RRT | 0 Week | 2 Weeks |
|---|---|---|---|
| Appearance | | Clear | Light Brown |
| Assay (% of initial conc.) | | 100.00 | 95.55 |
| % Racemization | | 0.63 | 0.62 |
| % Impurity F | 0.19 | 0.22 | 1.56 |
| % Synephrine | 1.26 | ND | ND |
| % Epinephrone | 1.36 | ND | ND |
| % Methoxy | 1.88 | 0.07 | 0.07 |
| % Unknown Impurity | 0.21 | ND | 0.12 |
| | 0.26 | ND | BQL |
| | 0.88 | ND | BQL |
| | 3.11 | ND | BQL |
| | 3.26 | ND | BQL |
| % Total Impurities | | 0.29 | 1.75 |

TABLE 10

Stability Data for Epinephrine Spray Formulation #9 stored at 40° C. ± 2° C./75% ± 5% Relative Humidity

| 40° C. Formulation #9 | RRT | 0 Week | 1 Week | 4 Weeks |
|---|---|---|---|---|
| Appearance | | Clear | Clear | Clear |
| Assay (% of initial conc.) | | 100.00 | 100.76 | 99.73 |
| % Racemization | | 0.60 | 0.68 | — |
| % Impurity F | 0.19 | 0.15 | 0.84 | 1.86 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | ND | ND | 0.06 |
| | 3.11 | ND | BQL | 0.09 |
| | 3.26 | ND | BQL | 0.08 |
| % Total Impurities | | 0.22 | 0.91 | 2.16 |

TABLE 11

Stability Data for Epinephrine Spray Formulation #10 stored at 40° C. ± 2° C./75% ± 5% Relative Humidity

| 40° C. Formulation #10 | RRT | 0 Week | 1 Week |
|---|---|---|---|
| Appearance | | Clear | Clear |
| Assay (% of initial conc.) | | 100.00 | 100.76 |
| % Racemization | | 0.60 | 0.68 |
| % Impurity F | 0.19 | 0.12 | 2.89 |
| % Synephrine | 1.26 | ND | ND |
| % Epinephrone | 1.36 | ND | ND |
| % Methoxy | 1.88 | 0.07 | 0.07 |
| % Unknown Impurity | 0.21 | ND | BQL |
| | 3.11 | ND | BQL |
| | 3.26 | ND | BQL |
| % Total Impurities | | 0.19 | 2.96 |

TABLE 12

Stability Data for Epinephrine Spray Formulation #11 stored at 40° C. ± 2° C./75% ± 5% Relative Humidity

| 40° C. Formulation #11 | RRT | 0 Week | 1 Week |
|---|---|---|---|
| Appearance | | Clear | Clear |
| Assay (% of initial conc.) | | 100.00 | 100.76 |
| % Racemization | | 0.60 | 0.68 |
| % Impurity F | 0.19 | 0.12 | 0.90 |
| % Synephrine | 1.26 | ND | ND |
| % Epinephrone | 1.36 | ND | ND |
| % Methoxy | 1.88 | 0.07 | 0.07 |
| % Unknown Impurity | 0.21 | ND | BQL |
| | 3.11 | ND | BQL |
| | 3.26 | ND | BQL |
| % Total Impurities | | 0.19 | 0.97 |

TABLE 13

Stability Data for Epinephrine Spray Formulation #1 stored at 25° C. ± 2° C./60% ± 5% Relative Humidity

| 25° C. Formulation #1 | RRT | 0 Week | 1 Month | 3 Months |
|---|---|---|---|---|
| Appearance | | Clear | Clear | Clear |
| Assay (% of initial conc.) | | 100.00 | 97.91 | 97.32 |
| % Racemization | | 0.60 | 0.76 | 0.93 |
| % Impurity F | 0.19 | 0.13 | 0.53 | 1.04 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | ND | 0.05 | 0.19 |
| | 3.11 | ND | ND | BQL |
| | 3.26 | ND | ND | BQL |
| % Total Impurities | | 0.20 | 0.65 | 1.30 |

TABLE 14

Stability Data for Epinephrine Spray Formulation #2 stored at 25° C. ± 2° C./60% ± 5% Relative Humidity

| 25° C. Formulation #2 | RRT | 0 Week | 1 Month | 3 Months |
|---|---|---|---|---|
| Appearance | | Clear | Clear | Clear |
| Assay (% of initial conc.) | | 100.00 | 97.56 | 96.88 |
| % Racemization | | 0.60 | 0.78 | 1.01 |
| % Impurity F | 0.19 | 0.14 | 0.55 | 1.25 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | ND | 0.08 | 0.18 |
| | 3.11 | ND | ND | BQL |
| | 3.26 | ND | ND | BQL |
| % Total Impurities | | 0.21 | 0.70 | 1.50 |

TABLE 15

Stability Data for Epinephrine Spray Formulation #3 stored at 25° C. ± 2° C./60% ± 5% Relative Humidity

| 25° C. Formulation #3 | RRT | 0 Week | 1 Month | 3 Months |
|---|---|---|---|---|
| Appearance | | Clear | Clear | Clear |
| Assay (% of initial conc.) | | 100.00 | 99.32 | 98.16 |
| % Racemization | | 0.60 | 0.75 | 0.84 |
| % Impurity F | 0.19 | 0.13 | 0.52 | 1.29 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | ND | BQL | 0.09 |
| | 3.11 | ND | ND | BQL |
| | 3.26 | ND | ND | BQL |
| % Total Impurities | | 0.20 | 0.59 | 1.45 |

TABLE 16

Stability Data for Epinephrine Spray Formulation #4 stored at 25° C. ± 2° C./60% ± 5% Relative Humidity

| | | 25° C. Formulation #4 | | | | | |
|---|---|---|---|---|---|---|---|
| | RRT | 0 Week | 3 Weeks | 4 Weeks | 8 Weeks | 3 Months | 6 Months |
| Appearance | | Clear | Clear | Clear | Clear | Clear | Clear |
| Assay (% of initial conc.) | | 100.00 | 100.76 | 99.79 | 99.31 | 99.09 | 98.69 |
| % Racemization | | 0.60 | 0.68 | — | 0.91 | 0.97 | — |
| % Impurity F | 0.19 | 0.15 | 0.41 | 0.50 | 1.01 | 1.46 | 2.39 |
| % Synephrine | 1.26 | ND | ND | ND | ND | ND | ND |
| % Epinephrone | 1.36 | ND | ND | ND | ND | BQL | BQL |
| % Methoxy | 1.88 | 0.08 | 0.08 | 0.08 | 0.08 | 0.08 | 0.08 |
| % Unknown Impurity | 0.21 | ND | 0.05 | 0.06 | 0.06 | 0.11 | 0.10 |
| | 3.02 | ND | ND | ND | ND | ND | 0.12 |
| | 3.11 | ND | ND | ND | ND | ND | 0.12 |
| | 3.26 | ND | ND | ND | ND | ND | 0.10 |
| % Total Impurities | | 0.23 | 0.54 | 0.64 | 1.15 | 1.65 | 2.91 |

TABLE 17

Stability Data for Epinephrine Spray Formulation #5 stored at 25° C. ± 2° C./60% ± 5% Relative Humidity

| 25° C. Formulation #5 | RRT | 0 Week | 1 Month | 3 Months |
|---|---|---|---|---|
| Appearance | | Clear | Clear | Clear |
| Assay (% of initial conc.) | | 100.00 | 98.40 | 97.29 |
| % Racemization | | 0.60 | 0.77 | 0.84 |
| % Impurity F | 0.19 | 0.15 | 0.67 | 1.41 |
| % Synephrine | 1.26 | ND | ND | ND |
| % Epinephrone | 1.36 | ND | ND | ND |
| % Methoxy | 1.88 | 0.07 | 0.07 | 0.07 |
| % Unknown Impurity | 0.21 | ND | 0.05 | 0.18 |
| | 3.11 | ND | ND | BQL |
| | 3.26 | ND | ND | BQL |
| % Total Impurities | | 0.22 | 0.79 | 1.66 |

TABLE 18

Stability Data for Epinephrine Spray Formulation #6 stored at 25° C. ± 2° C./60% ± 5% Relative Humidity

| 25° C. Formulation #6 | RRT | 0 Week | 2 Weeks | 1 Month | 6 Months |
|---|---|---|---|---|---|
| Appearance | | Clear | Clear | Clear | Clear |
| Assay (% of initial conc.) | | 100.00 | 100.25 | 99.75 | 94.80 |
| % Impurity F | 0.19 | 0.15 | 0.45 | 0.76 | 2.93 |
| % Synephrine | 1.26 | ND | ND | ND | ND |
| % Epinephrone | 1.36 | ND | BQL | BQL | BQL |
| % Methoxy | 1.88 | BQL | BQL | BQL | BQL |
| % Unknown Impurity | 0.21 | ND | ND | BQL | 0.30 |
| | 0.26 | ND | ND | ND | 0.13 |
| | 0.88 | ND | ND | ND | 0.15 |
| | 2.58 | ND | ND | ND | 0.10 |
| | 3.11 | ND | ND | ND | 0.24 |
| | 3.26 | ND | ND | ND | 0.17 |
| % Total Impurities | | 0.15 | 0.45 | 0.76 | 4.02 |

TABLE 19

Stability Data for Epinephrine Spray Formulation #8 stored at 25° C. ± 2° C./60% ± 5% Relative Humidity

| 25° C. Formulation #8 | RRT | 0 Week | 1 Month |
|---|---|---|---|
| Appearance | | Clear | Clear |
| Assay (% of initial conc.) | | 100.00 | 99.21 |
| % Racemization | | 0.63 | 0.66 |
| % Impurity F | 0.19 | 0.22 | 0.64 |
| % Synephrine | 1.26 | ND | ND |
| % Epinephrone | 1.36 | ND | ND |
| % Methoxy | 1.88 | 0.07 | 0.07 |
| % Unknown Impurity | 0.21 | ND | 0.06 |
| | 3.11 | ND | BQL |
| | 3.26 | ND | BQL |
| % Total Impurities | | 0.29 | 0.77 |

TABLE 20

Stability Data for Epinephrine Spray Formulation #9 stored at 25° C. ± 2° C./60% ± 5% Relative Humidity

| 25° C. Formulation #9 | RRT | 0 Week | 1 Month | 6 Months |
|---|---|---|---|---|
| Appearance | | Clear | Clear | Clear |
| Assay (% of initial conc.) | | 100.00 | 99.64 | 98.88 |
| % Impurity F | 0.19 | 0.15 | 0.52 | 1.71 |
| % Synephrine | 1.26 | ND | ND | ND |
| % Epinephrone | 1.36 | ND | ND | ND |
| % Methoxy | 1.88 | 0.08 | 0.07 | 0.07 |
| % Unknown Impurity | 0.21 | ND | 0.05 | 0.07 |
| | 3.11 | ND | BQL | 0.09 |
| | 3.26 | ND | BQL | 0.08 |
| % Total Impurities | | 0.23 | 0.64 | 2.02 |

Formulations #1-#5 had less than 3% total impurities after 4 Weeks (1 Month) at 40° C.±2° C./75%±5% Relative Humidity and less than 1% total impurities after 4 Weeks (1 Month) at 25° C.±2° C./60%±5% relative humidity. Of Formulations #6-#8, only Formulation #8 was analyzed at 4 Weeks or later at 40° C. where 4.68% total impurities were found. Formulation #9 exhibited total impurities of 2.17% at 4 weeks 40° C. Formulation #11 exhibited total impurities of 1% at one week 40° C. The superior and surprising stability characteristics of the formulations of the present invention will allow the formulations to be effective when used by patients.

When compared with formulation 4, formulation 7 showed a faster generation of impurities and was not stable for more than a month at 40° C. Formulation 4 was stable for 4 months when stored at 40° C. which indicates that EDTA increases the stability of epinephrine formulations.

Example 3

Formulation #4 was further tested for stability during freeze-thaw cycling. Specifically, Formulation #4 was run through 3 cycles of −20° C. for 48 hours and then 25° C. for 48 hours, where the physical appearance of the formulation was recorded. The formulation remained clear and colorless throughout the entire freeze-thaw cycling indicating a stable formulation throughout.

Example 4

In order to determine the spray profile of Formulation #4, it was subjected to standardized droplet testing. A challenge of creating an epinephrine spray formulation is that it must be capable of producing spray droplets that are over 10 microns in diameter. Spray droplets of 10 microns or smaller could be inhaled into the lungs.

Droplet analysis was conducted using standard laser analysis procedures known by those of skill in the art. Droplet size distribution ($Dv_{10}$, $Dv_{50}$, $Dv_{90}$, and Span) was tested at two distances, 3 cm and 6 cm. $Dv_{10}$ refers to the droplet size at which 10% of the volume is smaller; $Dv_{50}$ refers to the median droplet size; $Dv_{90}$ refers to droplet size for which 90% of the total volume is smaller; Span refers to distribution span (Dv90−Dv10)/Dv50. %<10 μm refers to the percentage of the total volume that is made up of droplets less than 10 μm in diameter.

Spray pattern, specifically Dmin, Dmax, and ovality ratio were tested at two distances, 3 cm and 6 cm. Dmin refers to the shortest diameter of the spray pattern in mm, Dmax refers to the widest diameter of the spray pattern in mm, and ovality ratio refers to the ratio of Dmax to Dmin. The spay pattern is measured by shining a laser sheet perpendicular to the spray at a specific distance from the orifice. The ovality ratio is useful as it provides information regarding the shape and density of the spray pump plume.

The results of these tests can be seen below in Tables 17 to 22.

TABLE 21

Droplet size distribution of Epinephrine Spray Formulation at 3 cm

| Droplet Size Distribution 3 cm | $DV_{10}$ (μm) | $DV_{50}$ (μm) | $DV_{90}$ (μm) | % < 10 μm | Span |
|---|---|---|---|---|---|
| Min | 15.8 | 30.84 | 124 | 0.05 | 3.145 |
| Max | 17.23 | 33.96 | 228.7 | 0.89 | 6.283 |
| Mean | 16.34 | 32.88 | 177.9 | 0.473 | 4.93 |

TABLE 22

Droplet size distribution of Epinephrine Spray Formulation at 6 cm

| Droplet Size Distribution 6 cm | $DV_{10}$ (μm) | $DV_{50}$ (μm) | $DV_{90}$ (μm) | % < 10 μm | Span |
|---|---|---|---|---|---|
| Min | 22.72 | 36.07 | 59.52 | 0 | 1.017 |
| Max | 24.05 | 40.35 | 230.9 | 0 | 5.127 |
| Mean | 23.2 | 38.48 | 121.5 | 0 | 2.49 |

TABLE 23

Spray pattern of Epinephrine Spray Formulation at 3 cm

| Spray Pattern 3 cm | Dmin (mm) | Dmax (mm) | Ovality ratio |
|---|---|---|---|
| Min | 18.9 | 29.8 | 1.415 |
| Max | 22.2 | 32.1 | 1.696 |
| Mean | 20.4 | 31.1 | 1.53 |

TABLE 24

Spray pattern of Epinephrine Spray Formulation at 6 cm

| Spray Pattern 6 cm | Dmin (mm) | Dmax (mm) | Ovality ratio |
|---|---|---|---|
| Min | 26.5 | 47 | 1.68 |
| Max | 32.2 | 54.2 | 1.852 |
| Mean | 29.1 | 51.4 | 1.768 |

TABLE 25

Plume geometry of Epinephrine Spray Formulation at 3 cm

| Plume Geometry 3 cm | Angle (°) | Width (mm) |
|---|---|---|
| Min | 49.2 | 27.6 |
| Max | 63.4 | 37.8 |
| Mean | 55.4 | 32.2 |

TABLE 26

Plume geometry of Epinephrine Spray Formulation at 6 cm

| Plume Geometry 6 cm | Angle (°) | Width (mm) |
|---|---|---|
| Min | 37.7 | 37.7 |
| Max | 43.5 | 43.5 |
| Mean | 40.7 | 40.7 |

Applicant found during testing that formulations of the present invention yielded desirable droplet sizes for spray administration. The testing also revealed that the formulation dose remains consistent when administered with a spray pump.

Example 5. Preparation of Additional Hydro-Alcoholic Epinephrine Spray Formulations Additional epinephrine spray formulations were prepared using the components and amounts listed in Table 27 below. All solvents were purged with nitrogen prior to use. Excipients including 0.5 N or 1.0 N hydrochloric acid ("HCl"), ethanol, propylene glycol, EDTA, sodium bisulfite and/or caprylic acid were dissolved in water while stirring at room temperature. Epinephrine base was then added to the excipient solution. Finally, sodium hydroxide ("NaOH")/hydrochloric acid ("HCl") was used to adjust final pH.

TABLE 27

| Additional Hydro-alcoholic Epinephrine Spray Formulations | | | | | | | | | |
|---|---|---|---|---|---|---|---|---|---|
| % w/w | #12 | #13 | #14 | #15 | #16 | #17 | #18 | #19 | #20 |
| Epinephrine base | 3.2 | 3.2 | 3.2 | 3.2 | 3.2 | 3.38 | 3.38 | 3.24 | 3.12 |
| Hydrochloric acid (0.5N) | 34.6 | 34.6 | 34.6 | 34.6 | 34.6 | 37.7 | 37.7 | 36.2 | 34.8 |
| EDTA | 0.05 | 0.05 | 0.05 | 0.05 | 0.05 | 0.05 | 0.05 | 0.05 | 0.05 |
| Sodium bisulfite | 0.1 | 0.15 | 0.20 | 0.25 | 0.30 | 0.15 | 0.15 | 0.15 | 0.15 |
| Propylene Glycol | 5.0 | 5.0 | 5.0 | 5.0 | 5.0 | 5.0 | 5.0 | 5.0 | 5.0 |
| Caprylic acid | — | — | — | — | — | 2.0 | 10.0 | — | — |
| Benzalkonium chloride | — | — | — | — | — | 0.02 | 0.02 | 0.01 | 0.01 |
| Menthol | 1.0 | 1.0 | 1.0 | 1.0 | 1.0 | 0.5 | 0.5 | — | — |
| Sucralose | 0.5 | 0.5 | 0.5 | 0.5 | 0.5 | 0.5 | 0.5 | — | — |
| Ethanol | 40.0 | 40.0 | 40.0 | 40.0 | 40.0 | 40.0 | 40.0 | 40.0 | 20.0 |
| Water | 15.55 | 15.50 | 15.45 | 15.40 | 15.35 | 10.7 | 2.7 | 15.35 | 36.87 |
| pH adjusted with 2 NaOH/0.5N HCl | 4.5 | 4.5 | 4.5 | 4.5 | 4.5 | 4.5 | 4.5 | 4.5 | 4.5 |

TABLE 28

| Additional Aqueous based Epinephrine Spray Formulation | | | | | | |
|---|---|---|---|---|---|---|
| % w/w | #21 | #22 | #23 | #24 | #25 | #26 |
| Epinephrine base | 3.040 | 3.040 | 3.040 | 3.040 | 3.040 | 3.040 |
| Hydrochloric acid (0.5N) | 33.80 | 33.80 | 33.80 | 33.80 | 33.80 | 33.80 |
| EDTA | 0.05 | 0.05 | 0.05 | 0.05 | 0.05 | 0.05 |

TABLE 28-continued

Additional Aqueous based Epinephrine Spray Formulation

| % w/w | #21 | #22 | #23 | #24 | #25 | #26 |
|---|---|---|---|---|---|---|
| Sodium bisulfite | 0.150 | 0.250 | 0.5 | 1.00 | 2.00 | 5.00 |
| Benzalkonium chloride | 0.01 | 0.01 | 0.01 | 0.01 | 0.01 | 0.01 |
| Sodium Chloride | 0.6 | 0.6 | 0.6 | 0.6 | 0.6 | 0.6 |
| Water | 62.35 | 62.25 | 62.00 | 61.5 | 60.5 | 57.5 |
| pH adjusted with 2 NaOH/ 0.5N HCl | 4.5 | 4.5 | 4.5 | 4.5 | 4.5 | 4.5 |

TABLE 29

Additional Epinephrine (6 mg/spray) Formulations

| % w/w | Function | #27 | #28 | #29 | #30 |
|---|---|---|---|---|---|
| Epinephrine base | Active Ingredient | 5.923 | 6.356 | 5.923 | 6.356 |
| Benzalkonium chloride | Preservative | 0.010 | 0.010 | 0.010 | 0.010 |
| Sodium Chloride | Tonicity Agent | 0.600 | — | 0.600 | — |
| Sodium bisulfite | Anti-Oxidant | 0.150 | 0.150 | 0.300 | 0.300 |
| Edetate Disodium Dihydrate (EDTA) | Chelating agent | 0.050 | 0.050 | 0.050 | 0.050 |
| Hydrochloric acid (2N) | pH modifier | 16.462 | 17.736 | 16.462 | 17.736 |
| Purified Water | Vehicle | 76.805 | 30.698 | 76.655 | 30.548 |
| Dehydrated Alcohol (Ethanol) | Co-Solvent | — | 40.000 | — | 40.000 |
| Propylene Glycol Solution containing 2.0N NaOH and 0.5N HCl | Co-Solvent pH adjustment | — | 5.000 | — | 5.000 |
| | | Adjust to pH 4.5 ± 0.1 | Adjust to pH 4.5 ± 0.1 | Adjust to pH 4.5 ± 0.1 | Adjust to pH 4.5 ± 0.1 |

TABLE 30

Additional Epinephrine (9 mg/spray) Formulations

| % w/w | Function | #31 | #32 | #33 | #34 |
|---|---|---|---|---|---|
| Epinephrine base | Active Ingredient | 8.885 | 9.534 | 8.885 | 9.534 |
| Benzalkonium chloride | Preservative | 0.010 | 0.010 | 0.010 | 0.010 |
| Sodium Chloride | Tonicity Agent | 0.600 | — | 0.600 | — |
| Sodium bisulfite | Anti-Oxidant | 0.150 | 0.150 | 0.45 | 0.45 |
| Edetate Disodium Dihydrate (EDTA) | Chelating agent | 0.050 | 0.050 | 0.050 | 0.050 |
| Hydrochloric acid (2N) | pH modifier | 24.695 | 26.603 | 24.695 | 26.603 |
| Purified Water | Vehicle | 65.610 | 18.653 | 65.310 | 18.353 |
| Dehydrated Alcohol (Ethanol) | Co-Solvent | — | 40.000 | — | 40.000 |
| Propylene Glycol | Co-Solvent | — | 5.000 | — | 5.000 |
| Solution containing 2.0N NaOH and 0.5N HCl | pH adjustment | Adjust to pH 4.5 ± 0.1 | Adjust to pH 4.5 ± 0.1 | Adjust to pH 4.5 ± 0.1 | Adjust to pH 4.5 ± 0.1 |

TABLE 31

Epinephrine (3-5 mg/spray) Formulations

| % w/w | Function | #35 | #36 | #37 | #38 |
|---|---|---|---|---|---|
| Epinephrine base | Active Ingredient | 3.178 | 2.962 | 3.885 | 4.702 |
| Benzalkonium chloride | Preservative | 0.010 | 0.010 | 0.010 | 0.010 |
| Sodium Chloride | Tonicity Agent | — | 0.6 | — | — |
| Sodium bisulfite | Anti-Oxidant | 0.150 | 0.150 | 0.184 | 0.223 |
| Edetate Disodium Dihydrate (EDTA) | Chelating agent | 0.050 | 0.050 | 0.050 | 0.050 |
| Hydrochloric acid | pH modifier | 35.471 (0.5N) | 32.936 (0.5N) | 21.681 (1.0N) | 26.241 (1.0N) |
| Purified Water | Vehicle | 16.141 | 63.298 | 29.190 | 23.774 |
| Dehydrated Alcohol (Ethanol) | Co-Solvent | 40.000 | — | 40.000 | 40.000 |
| Propylene Glycol Solution containing 2.0N NaOH and 0.5N HCl | Co-Solvent pH adjustment | 5.000 Adjust to pH 4.5 ± 0.1 | — Adjust to pH 4.5 ± 0.1 | 5.000 | 5.000 |

The formulations listed in Table 27 and Table 28 were filled in unit dose devices, packed into an oxygen impermeable pouches with oxygen scavengers, and then subjected to stability at 40° C.±2° C./75%±5% relative humidity and 25° C.±2° C./60%±5% relative humidity. The stability of the formulations was analyzed at specified time points by evaluating their potency (assay value) and impurity levels. Assay and impurities were detected using high-performance liquid chromatography with an ultraviolet detector. The assay was performed at 280 nm and indicated as a % of initial concentration. For all impurities, analysis was performed at 210 nm and 280 nm and expressed as a % area. Amounts of particular impurities are listed in Tables 32 to 55 as a percentage of area of each formulation along with amount of total impurities. Relative retention time ("RRT") is given for each impurity. "ND" indicates that the impurity was not detected. Any impurity which is less than 0.05% is indicated as BQL. NP refers to Not Performed.

TABLE 32

Stability Data for Epinephrine Spray Formulations # 12 to # 16 stored at 25° C. ± 2° C./60% ± 5% Relative Humidity Stability @18 M 25° C./60% RH

|  | RRT | 0 Week | F # 12 18 months | F # 13 18 Months | F # 14 18 Months | F # 15 18 months | F # 16 18 months |
|---|---|---|---|---|---|---|---|
| Appearance |  | Clear | Clear | Clear | Clear | Clear | Clear |
| % Impurity F | 0.19 | 0.11 | 1.91 | 2.53 | 3.27 | 3.57 | 4.79* |
| % Synephrine | 1.26 | ND | ND | ND | ND | ND | ND |
| % Epinephrone | 1.36 | ND | BQL | BQL | BQL | BQL | BQL |
| % Methoxy | 1.90 | 0.07 | 0.08 | 0.08 | 0.07 | 0.07 | 0.08 |
| % Unknown Impurities | 0.22 | 0.01 | 0.12 | 0.12 | 0.13 | 0.12 | 0.12 |
|  | 0.25 | ND | 0.09 | BQL | BQL | ND | 0.07 |
|  | 0.26 | ND | ND | ND | ND | ND | ND |
|  | 0.64 | ND | ND | ND | ND | ND | BQL |
|  | 0.88 | ND | BQL | BQL | BQL | BQL | BQL |
|  | 1.21 | ND | 0.09 | 0.09 | 0.08 | BQL | 0.06 |
|  | 1.34 | ND | BQL | 0.05 | BQL | BQL | BQL |
|  | 1.50 | ND | ND | ND | 0.07 | BQL | BQL |
|  | 1.51 | ND | 0.1 | 0.07 | ND | ND | ND |
|  | 2.43 | ND | ND | ND | ND | 0.06 | ND |
|  | 2.44 | ND | ND | 0.07 | 0.08 | ND | ND |
|  | 2.45 | ND | 0.11 | ND | ND | ND | ND |
|  | 2.57 | ND | ND | ND | ND | ND | 0.06 |
|  | 2.71 | ND | ND | ND | ND | ND | ND |
|  | 2.90 | ND | ND | ND | BQL | ND | ND |
|  | 2.91 | ND | ND | BQL | ND | ND | ND |
|  | 2.93 | ND | 0.07 | ND | ND | ND | ND |
|  | 2.96 | ND | ND | ND | ND | ND | ND |
|  | 3.11 | ND | 0.05 | BQL | BQL | BQL | BQL |
|  | 3.26 | ND | ND | BQL | ND | ND | ND |
| Total Impurities |  | 0.19 | 2.62 | 3.01 | 3.70 | 3.82 | 5.18 |

TABLE 33

Stability Data for Epinephrine Spray Formulation # 17 stored at 25° C. ± 2° C./60% ± 5% Relative Humidity

|  | RRT | 1 Month | 2 Month |
|---|---|---|---|
| Appearance |  | Clear | Clear |
| % Impurity F | 0.19 | 0.50 | 0.72 |
| % Epinephrone | 1.36 | ND | ND |
| % Methoxy | 1.90 | 0.07 | 0.07 |
| % Unknown Impurities | 1.08 | 0.14 | 0.08 |
| % Total Impurities |  | 0.71 | 0.87 |

TABLE 34

Stability Data for Epinephrine Spray Formulation # 18 stored at 25° C. ± 2° C./60% ± 5% Relative Humidity

|  | RRT | 1 Month | 2 Months |
|---|---|---|---|
| Appearance |  | Clear | Clear |
| % Impurity F | 0.19 | 0.57 | 0.75 |
| % Epinephrone | 1.36 | ND | ND |
| % Methoxy | 1.90 | 0.07 | 0.07 |
|  | 1.08 | 0.08 | 0.14 |
|  | 1.12 | BQL | 0.07 |
| % Total Impurities |  | 0.72 | 1.03 |

TABLE 35

Stability Data for Epinephrine Spray Formulations # 19 stored at 25° C. ± 2° C./60% ± 5% Relative Humidity

| Epinephrine | RRT | T = 0 | 1 M | 3 M | 6 M | 12 M | 18 M |
|---|---|---|---|---|---|---|---|
| Assay (%) |  | 101.32 | 99.22 | 100.49 | 98.92 | 100.41 | 98.60 |
| Appearance |  | Clear, Colorless | Clear, Colorless | Clear, Colorless | Clear, Colorless | Clear, Colorless | Clear, Colorless |
| % Impurity F | 0.19 | 0.16 | 0.47 | 1.03 | 2.37 | 5.38 | 7.44 |
| % Epinephrone | 1.34 | ND | BQL | BQL | BQL | BQL | BQL |
| % Methoxy | 1.77 | 0.07 | 0.06 | 0.06 | 0.06 | 0.05 | 0.06 |
| Unknown Impurities (%) | 0.20 | ND | ND | 0.06 | 0.15 | 0.08 | 0.09 |
|  | 0.21 | ND | ND | ND | ND | 0.07 | 0.05 |
|  | 0.26 | ND | ND | ND | 0.08 | 0.16 | 0.20 |

TABLE 35-continued

Stability Data for Epinephrine Spray Formulations # 19 stored at 25° C. ± 2° C./60% ± 5% Relative Humidity

| Epinephrine | RRT | T = 0 | 1 M | 3 M | 6 M | 12 M | 18 M |
|---|---|---|---|---|---|---|---|
| | 1.06 | ND | ND | ND | ND | ND | 0.13 |
| | 1.20 | ND | ND | ND | 0.09 | 0.05 | 0.05 |
| | 2.50 | ND | ND | ND | ND | BQL | 0.06 |
| Total impurities (%) | | 0.23 | 0.53 | 1.15 | 2.75 | 5.79 | 8.08 |

TABLE 36

Stability Data for Epinephrine Spray Formulation # 20 stored at 25° C. ± 2° C./60% ± 5% Relative Humidity

| Epinephrine | RRT | T = 0 | 1M | 3M | 6M |
|---|---|---|---|---|---|
| Assay (% LC) | | 103.9307 | 102.23 | 99.07 | 97.70 |
| Appearance | | Clear, Colorless | Clear, Colorless | Clear, Colorless | Clear, Colorless |
| Imp-F | 0.19 | 0.16 | 0.53 | 1.25 | 2.86 |
| epinephrone | 1.35 | ND | BQL | BQL | BQL |
| Methoxy | 1.78 | 0.06 | 0.06 | 0.06 | 0.06 |
| Unknown | 0.21 | ND | ND | 0.05 | 0.05 |
| Impurities | 0.26 | ND | ND | ND | BQL |
| | 0.70 | ND | BQL | BQL | BQL |
| | 0.83 | ND | BQL | BQL | ND |
| | 0.88 | BQL | BQL | BQL | ND |
| | 1.22 | ND | ND | ND | BQL |
| | 1.41 | ND | ND | BQL | BQL |
| | 1.49 | ND | ND | ND | ND |
| | 1.51 | BQL | ND | ND | ND |
| | 1.55 | ND | BQL | BQL | ND |
| | 2.55 | ND | BQL | BQL | ND |
| | 2.56 | ND | BQL | BQL | ND |
| | 2.61 | ND | BQL | BQL | ND |
| | 2.72 | ND | ND | BQL | BQL |
| | 2.80 | ND | ND | BQL | ND |
| | 2.87 | ND | ND | ND | ND |
| | 2.96 | ND | BQL | ND | ND |
| | 3.09 | BQL | BQL | ND | ND |
| | 3.22 | ND | ND | BQL | ND |
| | 3.45 | ND | ND | BQL | ND |
| | 3.73 | ND | ND | ND | BQL |
| Total impurities (%) | | 0.22 | 0.59 | 1.36 | 2.97 |

TABLE 37

Stability Data for Epinephrine Spray Formulation # 21 stored at 25° C. ± 2° C./60% ± 5% Relative Humidity

| | RRT | T = 0 | 1 M | 2 M | 3 M | 4 M | 6 M | 8 M | 12 M |
|---|---|---|---|---|---|---|---|---|---|
| Assay | | 98.20 | 101.02 | 99.07 | 100.13 | 98.45 | 98.45 | 98.45 | 95.12 |
| Appearance | | Clear, Colorless | Clear, Colorless | Clear, Colorless | Clear, Colorless | Clear, Colorless | Clear, Colorless | Clear, Colorless | Clear, Colorless |
| % Impurity F | 0.19 | 0.16 | 0.72 | 1.38 | 1.99 | 2.54 | 4.30 | 5.40 | 7.05 |
| % Epinephrone | 1.34 | ND | BQL | BQL | BQL | BQL | BQL | BQL | BQL |
| % Methoxy | 1.77 | 0.06 | 0.06 | 0.06 | 0.06 | 0.06 | 0.05 | 0.05 | 0.05 |
| Unknown | 0.20 | ND | ND | ND | ND | ND | ND | BQL | BQL |
| Impurities | 0.66 | ND | ND | ND | ND | ND | ND | ND | 0.05 |
| Total impurities (%) | | 0.22 | 0.78 | 1.44 | 2.05 | 2.60 | 4.35 | 5.45 | 7.15 |

TABLE 38

Stability Data for Epinephrine Spray Formulations # 12 to 16 stored at 40° C. ± 2° C./75% ± 5% Relative Humidity

| | | Epinephrine | | | | | |
|---|---|---|---|---|---|---|---|
| | RRT | 0 Week | F# 12 2 Months | F# 13 2 Months | F# 14 2 Months | F# 15 2 Months | F# 16 2 Months |
| Assay | | 100.00 | 98.13 | 94.51 | 93.02 | 93.26 | 92.02 |
| Appearance | | Clear | Clear | Clear | Clear | Clear | Clear |
| % Impurity F | 0.19 | 0.11 | 3.22 | 5.64 | 7.42 | 9.7 | 11.3 |
| % Synephrine | 1.26 | ND | ND | ND | ND | ND | ND |
| % Epinephrone | 1.36 | ND | BQL | BQL | BQL | BQL | BQL |
| % Methoxy | 1.90 | 0.07 | 0.06 | 0.06 | 0.06 | 0.06 | 0.06 |
| % Unknown | 0.22 | BQL | 0.16 | 0.16 | 0.15 | 0.14 | 0.12 |
| Impurities | 0.25 | ND | 0.06 | 0.06 | 0.05 | 0.05 | 0.05 |
| | 0.26 | ND | ND | BQL | BQL | BQL | BQL |

TABLE 38-continued

Stability Data for Epinephrine Spray Formulations # 12 to 16 stored at 40° C. ± 2° C./75% ± 5% Relative Humidity

| | | Epinephrine | | | | |
|---|---|---|---|---|---|---|
| RRT | 0 Week | F# 12 2 Months | F# 13 2 Months | F# 14 2 Months | F# 15 2 Months | F# 16 2 Months |
| 0.88 | ND | ND | BQL | BQL | BQL | BQL |
| 1.21 | ND | 0.06 | 0.06 | 0.05 | BQL | BQL |
| 1.34 | ND | BQL | BQL | BQL | BQL | BQL |
| 1.55 | ND | BQL | BQL | BQL | BQL | BQL |
| 2.57 | ND | 0.18 | 0.11 | 0.1 | 0.08 | 0.07 |
| 3.11 | ND | BQL | BQL | BQL | BQL | BQL |
| 3.26 | ND | BQL | BQL | BQL | BQL | ND |
| % Total Impurities | 0.18 | 3.74 | 6.09 | 7.83 | 10.03 | 11.60 |

TABLE 39

Stability Data for Epinephrine Spray Formulations # 17 stored at 40° C. ± 2° C./75% ± 5% Relative Humidity

| | RRT | 2 Weeks | 4 Weeks | 6 Weeks | 3 Months |
|---|---|---|---|---|---|
| Physical appearance | | Clear | Clear | Clear | Clear |
| % Impurity F | 0.19 | 1.02 | 2.03 | 3.01 | 5.11 |
| % Epinephrone | 1.36 | ND | ND | BQL | BQL |
| % Methoxy | 1.90 | 0.07 | 0.07 | 0.07 | 0.06 |
| | 1.08 | 0.08 | 0.15 | 0.15 | 0.09 |
| | 1.12 | ND | ND | 0.15 | 0.15 |
| | 1.21 | ND | BQL | 0.06 | 0.13 |
| | 2.53 | BQL | BQL | 0.05 | 0.15 |
| | 2.58 | ND | ND | BQL | 0.06 |
| | 3.04 | ND | ND | BQL | 0.06 |
| % Total Impurities | | 1.17 | 2.25 | 3.49 | 5.81 |

TABLE 40

Stability Data for Epinephrine Spray Formulations # 18 stored at 40° C. ± 2° C./75% ± 5% Relative Humidity

| | RRT | 2 Weeks | 1 Month | 2 Months |
|---|---|---|---|---|
| Appearance | | Clear | Clear | Clear |
| % Impurity F | 0.19 | 0.93 | 2.16 | 3.71 |
| % Epinephrone | 1.36 | ND | BQL | BQL |
| % Methoxy | 1.90 | 0.07 | 0.07 | 0.07 |
| | 1.08 | 0.09 | 0.09 | 0.10 |
| | 1.12 | BQL | 0.06 | 0.14 |
| | 1.21 | ND | BQL | 0.18 |
| | 2.53 | 0.09 | 0.23 | 0.17 |
| | 2.58 | BQL | 0.08 | 0.07 |
| | 3.04 | BQL | BQL | 0.05 |
| % Total Impurities | | 1.18 | 2.69 | 4.49 |

TABLE 41

Stability Data for Epinephrine Spray Formulation # 19 stored at 40° C. ± 2° C./75% ± 5% Relative Humidity

| Epinephrine | RRT | 0 Month | 1 M | 2 M | 3 M | 4 M | 5 M | 6 M | 10 M |
|---|---|---|---|---|---|---|---|---|---|
| Assay | | 101.32 | 101.11 | 97.06 | 95.85 | 96.08 | 96.52 | 95.58 | NP |
| Appearance | | Clear, colorless | Clear, colorless | Clear, colorless | Clear, Light Yellow | Clear, Light Yellow | Clear, Light Yellow | Clear, Light Yellow | Clear, Light Yellow |
| Imp-F | 0.19 | 0.16 | 1.92 | 4.25 | 6.42 | 7.20 | 7.28 | 7.22 | 7.61 |
| epinephrone | 1.34 | ND | BQL | BQL | BQL | BQL | BQL | BQL | BQL |
| Methoxy | 1.77 | 0.07 | 0.06 | 0.06 | 0.06 | 0.06 | 0.06 | 0.06 | 0.06 |
| Unknown | 0.21 | ND | 0.09 | 0.19 | 0.11 | 0.3 | 0.07 | 0.14 | 0.18 |
| Impurities (%) | 0.26 | ND | ND | 0.14 | 0.21 | 0.31 | 0.32 | 0.31 | 0.52 |
| | 0.52 | ND | ND | ND | ND | BQL | BQL | BQL | BQL |
| | 0.64 | ND | ND | ND | ND | BQL | ND | ND | ND |
| | 0.79 | ND | ND | ND | BQL | ND | ND | BQL | BQL |
| | 0.88 | ND | BQL | ND | ND | BQL | BQL | BQL | BQL |
| | 1.17 | ND | 0.06 | 0.07 | 0.05 | 0.09 | 0.08 | ND | ND |
| | 1.25 | ND | BQL | BQL | BQL | BQL | 0.07 | 0.07 | 0.07 |
| | 1.38 | ND | BQL | BQL | BQL | BQL | BQL | BQL | BQL |
| | 1.55 | ND | ND | ND | BQL | ND | ND | ND | ND |
| | 1.68 | ND | ND | ND | BQL | BQL | BQL | BQL | BQL |
| | 1.73 | ND | ND | ND | BQL | BQL | BQL | BQL | BQL |
| | 1.99 | ND | ND | ND | ND | BQL | BQL | BQL | BQL |
| | 2.07 | ND | ND | ND | ND | BQL | BQL | BQL | BQL |
| | 2.38 | ND | BQL | ND | ND | ND | BQL | ND | ND |
| | 2.22 | ND | ND | ND | ND | ND | ND | BQL | BQL |
| | 2.44 | ND | ND | ND | ND | ND | ND | BQL | BQL |
| | 2.60 | ND | BQL | 0.05 | 0.1 | 0.19 | 0.33 | 0.76 | 0.99 |
| | 2.80 | ND | ND | ND | BQL | ND | ND | ND | ND |

TABLE 41-continued

Stability Data for Epinephrine Spray Formulation # 19 stored at 40° C. ± 2° C./75% ± 5% Relative Humidity

| Epinephrine | RRT | 0 Month | 1 M | 2 M | 3 M | 4 M | 5 M | 6 M | 10 M |
|---|---|---|---|---|---|---|---|---|---|
| | 2.86 | ND | BQL | ND | ND | ND | ND | ND | ND |
| | 2.98 | ND | BQL | ND | ND | ND | BQL | ND | ND |
| | 3.13 | ND | BQL | ND | ND | ND | ND | ND | ND |
| | 3.22 | ND | ND | ND | BQL | ND | ND | ND | ND |
| | 2.82 | ND | ND | ND | ND | 0.07 | 0.12 | 0.13 | 0.21 |
| | 3.38 | ND | ND | ND | ND | BQL | ND | ND | ND |
| | 3.41 | ND | ND | ND | ND | ND | BQL | ND | ND |
| | 3.44 | ND | ND | ND | BQL | 0.14 | 0.06 | ND | ND |
| | 3.51 | ND | ND | ND | ND | ND | ND | 0.13 | 0.12 |
| | 3.68 | ND | ND | ND | BQL | BQL | BQL | 0.07 | 0.06 |
| Total impurities (%) | | 0.23 | 2.13 | 4.76 | 6.95 | 8.36 | 8.39 | 8.89 | 9.82 |

TABLE 42

Stability Data for Epinephrine Spray Formulation # 20 stored at 40° C. ± 2° C./75% ± 5% Relative Humidity

| Epinephrine | RRT | T = 0 | 1 M | 2 M | 3 M | 4 M | 5 M | 6 M |
|---|---|---|---|---|---|---|---|---|
| Assay (%) | | 103.93 | 99.44 | 96.16 | 96.35 | 96.38 | 96.05 | 93.96 |
| Appearance | | Clear, colorless | Clear, colorless | Clear, colorless | Clear, Light Yellow | Clear, Light Yellow | Clear, Light Yellow | Clear, Light Yellow |
| % Impurity F | 0.19 | 0.16 | 2.61 | 5.66 | 7.69 | 6.30 | 7.42 | 7.67 |
| % Epinephrone | 1.35 | ND | BQL | BQL | BQL | BQL | BQL | BQL |
| % Methoxy | 1.78 | 0.06 | 0.07 | 0.06 | 0.06 | 0.06 | 0.07 | 0.07 |
| Unknown | 0.21 | ND | 0.08 | 0.10 | 0.09 | 0.29 | 0.10 | 0.13 |
| Impurities (%) | 0.26 | ND | ND | 0.06 | 0.12 | 0.17 | 0.18 | 0.19 |
| | 0.70 | ND | BQL | BQL | BQL | BQL | ND | BQL |
| | 0.88 | BQL | BQL | BQL | BQL | BQL | BQL | BQL |
| | 1.13 | ND | ND | ND | ND | ND | 0.08 | ND |
| | 1.18 | ND | BQL | BQL | BQL | 0.11 | ND | ND |
| | 1.21 | ND | ND | ND | ND | ND | ND | 0.06 |
| | 1.34 | ND | ND | ND | ND | BQL | BQL | ND |
| | 1.36 | ND | ND | ND | BQL | BQL | ND | BQL |
| | 1.49 | ND | BQL | ND | ND | ND | ND | ND |
| | 1.42 | ND | ND | ND | BQL | ND | ND | ND |
| | 1.51 | BQL | ND | ND | ND | ND | ND | ND |
| | 1.55 | ND | BQL | BQL | BQL | ND | ND | ND |
| | 1.58 | ND | ND | ND | ND | 0.09 | ND | ND |
| | 1.64 | ND | ND | ND | BQL | ND | ND | ND |
| | 1.73 | ND | ND | ND | ND | ND | BQL | 0.05 |
| | 1.89 | ND | ND | ND | BQL | ND | BQL | ND |
| | 2.00 | ND | ND | ND | ND | BQL | 0.05 | 0.08 |
| | 2.09 | ND | ND | ND | ND | ND | ND | 0.08 |
| | 2.21 | ND | ND | ND | ND | ND | ND | 0.08 |
| | 2.39 | ND | BQL | ND | ND | BQL | BQL | ND |
| | 2.44 | ND | ND | ND | ND | ND | ND | 0.05 |
| | 2.56 | ND | BQL | ND | ND | ND | BQL | BQL |
| | 2.61 | ND | BQL | BQL | 0.07 | ND | ND | ND |
| | 2.71 | ND | ND | ND | ND | 0.39 | 0.54 | 1.10 |
| | 2.87 | ND | BQL | ND | BQL | BQL | ND | ND |
| | 2.96 | ND | BQL | ND | ND | ND | ND | BQL |
| | 3.09 | BQL | BQL | ND | ND | ND | ND | ND |
| | 3.14 | ND | BQL | ND | ND | ND | ND | ND |
| | 3.36 | ND | ND | ND | 0.14 | 0.16 | 0.16 | 0.17 |
| | 3.48 | ND | ND | ND | ND | 0.22 | 0.04 | 0.19 |
| | 3.55 | ND | ND | ND | BQL | BQL | ND | BQL |
| | 3.71 | ND | ND | 0.05 | ND | ND | 0.05 | 0.08 |
| | 3.83 | ND | ND | ND | ND | ND | ND | BQL |
| | 4.34 | ND | ND | ND | ND | ND | ND | BQL |
| Total impurities (%) | | 0.22 | 2.76 | 5.93 | 8.17 | 7.79 | 8.69 | 10.00 |

TABLE 43

Stability Data for Epinephrine Spray Formulation # 21 stored at 40° C. ± 2° C./75% ± 5% Relative Humidity

| Epinephrine | RRT | T = 0 | 1 M | 2 M | 3 M | 4 M | 5 M | 8 M | 12 M |
|---|---|---|---|---|---|---|---|---|---|
| Assay (%) | | 98.20 | 94.84 | 94.14 | 95.37 | 95.07 | 95.87 | 95.18 | 96.1 |
| Appearance | | Clear, colorless | Clear, colorless | Clear, Light Yellow | Clear, Light Yellow | Clear, Light Yellow | Clear, Light Yellow | Clear, Light Yellow | Clear, Light Yellow |
| % Impurity F | 0.19 | 0.16 | 4.43 | 7.96 | 8.20 | 8.31 | 7.93 | 8.47 | 8.36 |
| % Epinephrone | 1.34 | ND | BQL | BQL | BQL | BQL | BQL | BQL | BQL |
| % Methoxy | 1.77 | 0.06 | 0.06 | 0.06 | 0.06 | 0.05 | 0.09 | 0.05 | 0.05 |
| Unknown | 0.20 | ND | 0.06 | ND | ND | 0.11 | 0.11 | BQL | BQL |
| Impurities (%) | 0.66 | ND | ND | ND | ND | ND | BQL | BQL | BQL |
| | 0.83 | ND | ND | ND | ND | ND | ND | 0.05 | ND |
| | 1.67 | ND | ND | ND | 0.15 | 0.14 | 0.14 | 0.11 | 0.12 |
| | 1.70 | ND | ND | ND | ND | ND | ND | ND | 0.08 |
| | 1.73 | ND | ND | ND | ND | ND | 0.07 | 0.06 | 0.13 |
| | 1.81 | ND | ND | ND | ND | ND | ND | 0.08 | 0.05 |
| | 1.82 | ND | ND | ND | ND | ND | ND | 0.06 | BQL |
| | 1.92 | ND | ND | ND | ND | ND | ND | 0.08 | 0.31 |
| | 1.95 | ND | ND | ND | ND | ND | ND | 0.08 | 0.09 |
| | 2.00 | ND | ND | ND | ND | ND | ND | 0.06 | 0.1 |
| | 2.09 | ND | ND | ND | ND | ND | ND | 0.09 | 0.27 |
| | 2.27 | ND | ND | ND | ND | ND | ND | ND | 0.06 |
| | 2.40 | ND | ND | ND | ND | ND | ND | 0.24 | 0.29 |
| | 2.72 | ND | ND | ND | BQL | BQL | BQL | BQL | 0.08 |
| | 2.79 | ND | ND | ND | 0.17 | 0.18 | 0.26 | BQL | 0.57 |
| | 2.84 | BQL | BQL | ND | 0.05 | ND | 0.12 | 0.12 | 0.2 |
| | 2.87 | ND | ND | ND | ND | 0.2 | 0.13 | 0.12 | 0.62 |
| | 2.96 | ND | ND | ND | ND | ND | ND | ND | 0.08 |
| | 2.98 | ND | ND | ND | ND | ND | ND | ND | 0.11 |
| | 3.06 | ND | ND | ND | ND | ND | ND | ND | 0.14 |
| | 3.15 | ND | ND | ND | ND | ND | ND | ND | 0.08 |
| | 3.18 | ND | ND | ND | ND | ND | ND | ND | 0.06 |
| Total impurities (%) | | 0.22 | 4.55 | 8.02 | 8.63 | 8.99 | 8.85 | 9.67 | 11.85 |

TABLE 44

Stability Data for Epinephrine Spray Formulation # 27 stored at 40° C. ± 2° C./75% ± 5% Relative Humidity

| | RRT | T = 0 | 1 M | 3 M | 4 M |
|---|---|---|---|---|---|
| Appearance | | Clear, colorless | Clear, colorless | Clear, Light Yellow | Clear, Light Yellow |
| Assay | | 101.98 | 101.74 | NP | NP |
| % Impurity F | 0.19 | 0.16 | 3.36 | 3.26 | 3.49 |
| % Epinephrone | 1.34 | BQL | BQL | BQL | BQL |
| % Methoxy | 1.77 | 0.06 | 0.06 | 0.08 | 0.08 |
| Unknown (%)Impurities | 0.20 | ND | 0.05 | 0.05 | 0.06 |
| | 1.12 | ND | ND | 0.09 | 0.05 |
| | 2.14 | ND | ND | ND | 0.05 |
| | 2.34 | ND | ND | ND | 0.06 |
| | 2.89 | ND | ND | ND | 0.16 |
| | 2.96 | ND | ND | 0.50 | 0.48 |
| | 2.99 | ND | ND | 0.10 | 0.19 |
| | 3.05 | ND | 0.38 | 0.46 | 0.43 |
| Total impurities (%) | | 0.22 | 3.85 | 4.54 | 5.05 |

TABLE 45

Stability Data for Epinephrine Spray Formulation # 28 stored at 40° C. ± 2° C./75% ± 5% Relative Humidity

| | RRT | T = 0 | 1 M | 3 M | 4 M |
|---|---|---|---|---|---|
| Appearance | | Clear, colorless | Clear, colorless | Clear, Light Yellow | Clear, Light Yellow |
| Assay | | 108.90 | 107.20 | NP | NP |
| % Impurity F | 0.19 | 0.16 | 1.75 | 3.15 | 3.61 |
| % Epinephrone | 1.34 | BQL | BQL | BQL | BQL |
| % Methoxy | 1.77 | 0.06 | 0.06 | 0.08 | 0.08 |
| Unknown Impurities (%) | 0.20 | ND | 0.24 | 0.24 | 0.33 |
| | 0.25 | ND | ND | 0.09 | 0.09 |
| | 2.50 | ND | 0.10 | 0.25 | 0.83 |
| | 2.96 | ND | ND | 0.21 | 0.37 |
| | 2.99 | ND | ND | ND | 0.05 |
| | 3.05 | ND | 0.07 | 0.15 | 0.28 |
| | 3.21 | ND | ND | ND | 0.27 |
| Total impurities (%) | | 0.22 | 2.22 | 4.17 | 5.91 |

TABLE 46

Stability Data for Epinephrine Spray Formulation # 29 stored at 40° C. ± 2° C./75% ± 5% Relative Humidity

| | RRT | T = 0 | 1 M | 3 M | 4 M |
|---|---|---|---|---|---|
| Appearance | | Clear, colorless | Clear, colorless | Clear, Light Yellow | Clear, Light Yellow |
| Assay | | 101.08 | 102.42 | NP | NP |
| % Impurity F | 0.19 | 0.16 | 6.12 | 8.87 | 8.86 |

TABLE 46-continued

Stability Data for Epinephrine Spray Formulation # 29 stored at 40° C. ± 2° C./75% ± 5% Relative Humidity

|  | RRT | T = 0 | 1 M | 3 M | 4 M |
|---|---|---|---|---|---|
| % Epinephrone | 1.34 | BQL | BQL | BQL | BQL |
| % Methoxy | 1.77 | 0.06 | 0.06 | 0.06 | 0.08 |
| Unknown | 0.20 | ND | BQL | BQL | BQL |
| Impurities | 0.25 | ND | ND | ND | ND |
|  | 1.06 | ND | ND | ND | 0.14 |
|  | 1.12 | ND | ND | 0.09 | 0.09 |
|  | 1.99 | ND | ND | 0.06 | 0.12 |
|  | 2.05 | ND | ND | ND | 0.14 |
|  | 2.15 | ND | ND | ND | 0.08 |
|  | 2.34 | ND | ND | ND | 0.08 |
|  | 2.89 | ND | ND | 0.11 | 0.23 |
|  | 2.96 | ND | ND | 0.45 | 0.47 |
|  | 2.99 | ND | ND | 0.13 | 0.27 |
|  | 3.05 | BQL | BQL | 0.40 | 0.43 |
|  | 3.20 | ND | ND | 0.15 | 0.23 |
| Total impurities (%) |  | 0.22 | 6.18 | 10.32 | 11.22 |

TABLE 47

Stability Data for Epinephrine Spray Formulation # 30 stored at 40° C. ± 2° C./75% ± 5% Relative Humidity

|  | RRT | T = 0 | 1 M | 3 M | 4 M |
|---|---|---|---|---|---|
| Appearance |  | Clear, colorless | Clear, colorless | Clear, Light Yellow | Clear, Light Yellow |
| Assay |  | 106.62 | 107.37 | NP | NP |
| % Impurity F | 0.19 | 0.16 | 5.00 | 8.76 | 8.41 |
| % Epinephrone | 1.34 | BQL | BQL | BQL | BQL |
| % Methoxy | 1.77 | 0.06 | 0.06 | 0.09 | 0.08 |
| Unknown | 0.20 | ND | BQL | 0.07 | 0.07 |
| Impurities | 0.25 | ND | ND | 0.14 | 0.16 |
|  | 1.06 | ND | ND | ND | 0.14 |
|  | 1.12 | ND | ND | 0.05 | BQL |
|  | 2.50 | ND | 0.05 | 0.12 | 0.43 |
|  | 2.96 | ND | ND | 0.06 | 0.29 |
|  | 2.99 | ND | ND | ND | 0.07 |
|  | 3.05 | ND | BQL | 0.05 | 0.23 |
|  | 3.20 | ND | BQL | 0.05 | 0.16 |
| Total impurities (%) |  | 0.22 | 5.11 | 9.39 | 10.04 |

TABLE 48

Stability Data for Epinephrine Spray Formulation # 31 stored at 40° C. ± 2° C./75% ± 5% Relative Humidity

|  | RRT | T = 0 | 1 M | 3 M |
|---|---|---|---|---|
| Appearance |  | Clear, colorless | Clear, colorless | Clear, Light Yellow |
| Assay |  | 101.23 | 115.59 | NP |
| % Impurity F | 0.19 | 0.16 | 2.75 | 2.35 |
| % Epinephrone | 1.34 | BQL | BQL | BQL |
| % Methoxy | 1.77 | 0.06 | 0.06 | 0.09 |
| Unknown | 0.18 | ND | BQL | BQL |
| Impurities (%) | 1.12 | ND | ND | 0.05 |
|  | 2.03 | ND | ND | 0.05 |
|  | 2.79 | ND | ND | BQL |
|  | 2.86 | ND | ND | 0.12 |
|  | 2.92 | ND | ND | 0.82 |
|  | 2.99 | ND | 0.05 | 0.14 |
|  | 3.05 | ND | 0.92 | 0.72 |
|  | 3.16 | ND | ND | 0.08 |
| Total impurities (%) |  | 0.22 | 3.78 | 4.42 |

TABLE 49

Stability Data for Epinephrine Spray Formulation # 32 stored at 40° C. ± 2° C./75% ± 5% Relative Humidity

|  | RRT | T0 | 1 M | 3 M |
|---|---|---|---|---|
| Appearance |  | Clear, colorless | Clear, colorless | Clear, Light Yellow |
| Assay |  | 108.96 | 103.80 | NP |
| % Impurity F | 0.19 | 0.16 | 1.89 | 2.50 |
| % Epinephrone | 1.34 | BQL | BQL | BQL |
| % Methoxy | 1.77 | 0.06 | 0.06 | 0.09 |
| Unknown | 0.18 | ND | 0.11 | 0.08 |
| Impurities | 0.25 | ND | ND | BQL |
|  | 1.12 | ND | ND | 0.07 |
|  | 1.19 | ND | ND | 0.05 |
|  | 2.48 | ND | 0.16 | 0.50 |
|  | 2.92 | ND | ND | 0.49 |
|  | 3.00 | ND | 0.16 | 0.37 |
|  | 3.16 | ND | ND | 0.16 |
| Total impurities (%) |  | 0.22 | 2.38 | 4.31 |

TABLE 50

Stability Data for Epinephrine Spray Formulation # 33 stored at 40° C. ± 2° C./75% ± 5% Relative Humidity

|  | RRT | T = 0 | 1 M | 3 M |
|---|---|---|---|---|
| Appearance |  | Clear, colorless | Clear, colorless | Clear, Light Yellow |
| Assay |  | 100.05 | 99.36 | NP |
| % Impurity F | 0.19 | 0.16 | 9.14 | 9.82 |
| % Epinephrone | 1.34 | BQL | BQL | BQL |
| % Methoxy | 1.77 | 0.06 | 0.06 | 0.09 |
| Unknown | 0.18 | ND | BQL | BQL |
| Impurities (%) | 1.74 | ND | ND | 0.60 |
|  | 1.98 | ND | ND | 0.07 |
|  | 2.04 | ND | ND | 0.07 |
|  | 2.32 | ND | ND | 0.07 |
|  | 2.86 | ND | ND | 0.18 |
|  | 2.92 | ND | ND | 0.70 |
|  | 2.95 | ND | ND | 0.23 |
|  | 3.01 | ND | ND | 0.62 |
|  | 3.16 | ND | ND | 0.15 |
|  | 3.29 | ND | ND | 0.05 |
| Total impurities (%) |  | 0.22 | 9.20 | 12.65 |

TABLE 51

Stability Data for Epinephrine Spray Formulation # 34 stored at 40° C. ± 2° C./75% ± 5% Relative Humidity

| Epinephrine | RRT | T = 0 | 1 M | 3 M |
|---|---|---|---|---|
| Appearance | | Clear, colorless | Clear, colorless | Clear Light Yellow |
| Assay | | 113.33 | 112.55 | NP |
| % Impurity F | 0.19 | 0.16 | 6.30 | 9.61 |
| % Epinephrone | 1.34 | BQL | BQL | BQL |
| % Methoxy | 1.77 | 0.06 | 0.06 | 0.08 |
| Unknown | 0.18 | ND | BQL | 0.06 |
| Impurities (%) | 0.25 | ND | ND | 0.09 |
| | 1.06 | ND | ND | 0.16 |
| | 1.12 | ND | ND | 0.07 |
| | 1.32 | ND | ND | BQL |
| | 2.32 | ND | ND | BQL |
| | 2.55 | ND | 0.07 | 0.23 |
| | 2.93 | ND | ND | 0.34 |
| | 2.96 | ND | ND | 0.07 |
| | 2.98 | ND | ND | 0.08 |
| | 3.02 | ND | 0.08 | 0.28 |
| | 3.17 | ND | ND | 0.08 |
| Total impurities (%) | | 0.22 | 6.51 | 11.15 |

TABLE 52

Stability Data for Epinephrine Spray Formulation # 35 stored at 40° C. ± 2° C./75% ± 5% Relative Humidity

| | RRT | T = 0 | 2 M | 3 M | 6 M |
|---|---|---|---|---|---|
| Assay | | 101.32 | 83.12 | 91.78 | 100.20 |
| Appearance | | Clear, colorless | Clear, colorless | Clear, colorless | Clear, colorless |
| % Impurity F | 0.19 | 0.16 | 4.56 | 6.40 | 7.56 |
| % Epinephrone | 1.34 | ND | BQL | BQL | BQL |
| % Methoxy | 1.77 | 0.07 | 0.06 | 0.05 | 0.05 |
| Unknown | 0.20 | ND | ND | ND | 0.13 |
| Impurities (%) | 0.21 | ND | 0.26 | 0.05 | 0.08 |
| | 0.26 | ND | 0.13 | 0.12 | 0.30 |
| | 1.19 | ND | 0.06 | BQL | BQL |
| | 1.71 | ND | BQL | BQL | 0.05 |
| | 1.95 | ND | ND | ND | 0.07 |
| | 2.45 | ND | 0.06 | 0.05 | 0.73 |
| | 2.92 | ND | ND | ND | 0.19 |
| | 2.95 | ND | ND | ND | 0.13 |
| | 2.97 | ND | ND | ND | 0.16 |
| Total Impurities (%) | | 0.23 | 5.13 | 6.67 | 9.45 |

TABLE 53

Stability Data for Epinephrine Spray Formulation # 36 stored at 40° C. ± 2° C./75% ± 5% Relative Humidity

| | RRT | T = 0 | 2 M | 6 M |
|---|---|---|---|---|
| Assay | | 101.32 | 91.40 | 103.10 |
| Appearance | | Clear, colorless | Clear, colorless | Clear, colorless |
| % Impurity F | 0.19 | 0.16 | 6.81 | 6.90 |
| % Epinephrone | 1.34 | ND | BQL | BQL |
| % Methoxy | 1.77 | 0.07 | 0.06 | 0.05 |
| Unknown | 0.21 | ND | 0.09 | 0.07 |
| Impurities (%) | 0.70 | ND | BQL | ND |
| | 1.71 | ND | ND | 0.07 |
| | 1.92 | ND | ND | 0.07 |
| | 1.95 | ND | ND | 0.05 |
| | 2.00 | ND | ND | 0.05 |
| | 2.09 | ND | ND | 0.06 |
| | 2.27 | ND | ND | 0.05 |
| | 2.41 | ND | ND | 0.08 |
| | 2.84 | ND | ND | 0.19 |
| | 2.90 | ND | ND | 0.29 |
| | 2.93 | ND | ND | 0.31 |
| | 2.98 | ND | ND | 0.25 |
| Total Impurities (%) | | 0.23 | 6.96 | 8.49 |

TABLE 54

Stability Data for Epinephrine Spray Formulation # 35 stored at 25° C. ± 2° C./60% ± 5% Relative Humidity

| | RRT | T = 0 | 3 M | 6 M |
|---|---|---|---|---|
| Assay | | 101.32 | 92.83 | 101.79 |
| Appearance | | Clear, colorless | Clear, colorless | Clear, colorless |
| % Impurity F | 0.19 | 0.16 | 1.08 | 2.32 |
| % Epinephrone | 1.34 | ND | BQL | BQL |
| % Methoxy | 1.77 | 0.07 | 0.05 | 0.06 |
| Unknown | 0.21 | ND | BQL | 0.07 |
| Impurities (%) | 0.26 | ND | ND | ND |
| | 0.23 | ND | ND | BQL |
| | 1.20 | ND | ND | BQL |
| | 2.45 | ND | ND | BQL |
| Total Impurities (%) | | 0.23 | 1.13 | 2.45 |

TABLE 55

Stability Data for Epinephrine Spray Formulation # 36 stored at 25° C. ± 2° C./60% ± 5% Relative Humidity

| | RRT | T = 0 | 3 M | 6 M |
|---|---|---|---|---|
| Assay | | 101.32 | 103.80 | 104.79 |
| Appearance | | Clear, colorless | Clear, colorless | Clear, colorless |
| % Impurity F | 0.19 | 0.16 | 1.54 | 4.00 |
| % Epinephrone | 1.34 | ND | BQL | BQL |
| % Methoxy | 1.77 | 0.07 | 0.06 | 0.05 |
| Unknown | 0.21 | ND | BQL | BQL |
| Impurities (%) | 0.72 | ND | BQL | BQL |
| | 0.83 | ND | BQL | ND |
| | 3.09 | ND | BQL | 0.05 |
| Total impurities (%) | | 0.23 | 1.60 | 4.10 |

All formulas exemplified in Tables 27 to 31 above, remained clear throughout stability testing. Formulations were filled in to unit dose spray devices under nitrogen blanket, and then subjected to accelerated stability testing at 25° C.±2° C./60%±5% and 40° C.±2° C./75%±5% without pouching (Formulations 12 to 18), while formulations (F#19 to 36) were subjected to accelerated stability testing under similar conditions with pouching containing oxygen scavenges. Formulation 13, un-pouched showed impurity F levels at 5.64% at 2M/40° C. However similar formulation 19, pouched, exhibited impurity F levels at 4.25% at 2M/40° C. Stability data suggest that epinephrine spray formulations which are pouched with oxygen scavenges are more stable compare to un-pouched formulations. Both hydro-alcoholic and aqueous formulations of present invention are stable at room temperature as well as 40° C.±2° C./75%±5.

For the Epinephrine 6 mg aqueous formulation in pouches, 3.49% and 8.86% of impurity F was observed after a period of 4 months at 40° C.±2° C./75% RH±5% RH for Formulations #27 and 29 respectively. Total impurities for Formulations #27 and 29 were found to be 5.05% and 11.22% after a period of 4 months at 40° C.±2° C./75% RH±5% RH, respectively. In the case of hydro-alcoholic formulations of the same strength in pouches, 3.61% and 8.41% of impurity F was observed after the same period for formulations #28 and 30, respectively. Total impurities for Formulations #28 and 30 were found to be 5.91% and 10.04% after a period of 4 months at 40° C.±2° C./75% RH±5% RH, respectively.

For the Epinephrine 9 mg aqueous formulation in pouches, 2.35% and 9.82% of impurity F was observed after a period of 4 months at 40° C.±2° C./75% RH±5% RH for Formulations #31 and 33 respectively. Total impurities for formulations #31 and 33 were found to be 4.42% and 12.65% after a period of 4 months at 40° C.±2° C./75% RH±5% RH, respectively. In the case of hydro-alcoholic formulations of the same strength in pouches, 2.50% and 9.61% of impurity F was observed after the same period for Formulations #32 and 34. Total impurities for Formulations #32 and 34 were found to be 4.31% and 11.15% after a period of 4 months at 40° C.±2° C./75% RH±5% RH, respectively.

Example 6. Mini-Pig Pharmacokinetic Data for Epinephrine Formulations

Protocol design was a single-dose crossover study. Five healthy male Yucatan mini-pigs weighing approximately eighty to ninety-five kilograms each were administered epinephrine formulations. The minipigs were fasted overnight till four hours' post administration. Each dosing was followed by a washout period of at least one-week. Blood samples were taken prior to administration and 2, 5, 10, 15, 20, 30, 45 min, 1, 1.5, 2, 4, and 24 hours' post dose. Minipig plasma samples were measured for epinephrine concentrations via liquid chromatography-tandem mass spectrometry.

The following pharmacokinetic parameters were calculated: peak concentration in plasma ($C_{max}$), time to reach $C_{max}$ ($T_{max}$), and area under the concentration-time curve from time-zero to 24 hours postdose ($AUC_{0\text{-}24\,h}$).

The pharmacokinetic behavior of epinephrine formulations was evaluated. At 5 minutes after a single-dose intramuscular (IM) administration of epinephrine in minipigs, the geometric mean plasma concentration of epinephrine was 0.046 ng/mL. When epinephrine was formulated in #M1 and administered intranasally, a more rapid absorption of epinephrine was observed. Specifically, #M1 showed a geometric mean epinephrine plasma concentration of 0.26 ng/mL at 5 minutes postdose. It was also noted that a plasma concentration of 0.41 ng/mL was achieved as early as 2 minutes after an intranasal administration of #M1. In addition, #M1 showed a geometric mean Cmax of 1.01 ng/mL and a geometric mean $AUC_{0\text{-}24\,h}$ of 161.0 ng*min/L.

TABLE 56

Epinephrine Formulations for Minipig Dosing

| Formulation | #M1 |
|---|---|
| Epinephrine base | 3.25 |
| Dilute Hydrochloric acid 0.5N | 36.2 |

TABLE 56-continued

Epinephrine Formulations for Minipig Dosing

| Formulation | #M1 |
|---|---|
| Benzalkonium Chloride | 0.01 |
| Ethanol | 40 |
| Propylene Glycol | 5 |
| Sodium Bisulfite | 0.15 |
| EDTA | 0.05 |
| Water | 15.34 |
| Total | 100 |

Components: % w/w

TABLE 57

Plasma concentrations for epinephrine after administration to Yucatan minipigs under fasted conditions.

| Formulation | IM solution | #M1 |
|---|---|---|
| Route of administration | IM | Intranasal |
| Dose per animal (mg) | 0.3 | 6 |
| Concentration @ 2 min (ng/mL) | 0.036 | 0.41 |
| Concentration @ 5 min (ng/mL) | 0.046 | 0.26 |
| Concentration @ 10 min (ng/mL) | 0.073 | 0.31 |
| Concentration @ 15 min (ng/mL) | 0.103 | 0.17 |
| Concentration @ 30 min (ng/mL) | 0.100 | 0.19 |
| $T_{max}$ (min) | 90 | 5 |
| $C_{max}$ (ng/mL) | 0.25 | 1.01 |
| $AUC_{0\text{-}24\,h}$ (ng * min/mL) | 173.7 | 161.0 |

Plasma concentration: geometric mean
$T_{max}$: median value
$C_{max}$ and $AUC_{0\text{-}24\,h}$: geometric mean Example 7. Rabbit Pharmacokinetic Data for Epinephrine Formulations Protocol design was a single-dose non-crossover study. Pharmacokinetics of a number of epinephrine formulations were evaluated in healthy male New Zealand white rabbits weighing approximately two to three kilograms. For dosing of each formulation, five or six rabbits were used. The rabbits were fasted overnight till four hours' post administration. Blood samples were taken prior to administration and 5, 10, 15, 20, 30, 40 min, 1, 1.5, 2, 4, and 5 hours' post dose. Rabbit plasma samples were measured for epinephrine concentrations via liquid chromatography-tandem mass spectrometry.

Formulation #R1-#R8 were provided in Table 43 and 44. Formulation #R9 existed as a spray-dried powder of epinephrine bitartrate salt. For the evaluation of #R9, approximately 21.83 mg of powder was dosed to each animal, as an equivalent dose of 12 mg epinephrine.

The following pharmacokinetic parameters were calculated: peak concentration in plasma ($C_{max}$), time to reach $C_{max}$ ($T_{max}$), and area under the concentration-time curve from time-zero to 24 hours postdose ($AUC_{0\text{-}24\,h}$).

The pharmacokinetic behavior of epinephrine formulations was evaluated. At 5 minutes after a single-dose IM administration of epinephrine in rabbits, the mean plasma concentration of epinephrine was 0.988 ng/mL. In comparison, a sublingual administration of #R9 enabled a similar absorption of epinephrine in the early phase. Specifically, #R9 showed a mean epinephrine plasma concentration of 0.0.814 ng/mL at 5 minutes postdose. It was also noted that a plasma concentration of 0.713 ng/mL was achieved at 5 minutes after a sublingual administration of #R6. In addition, #R9 showed a geometric mean Cmax of 7.0 ng/mL and a geometric mean AUC0-24 h of 1050.1 ng*min/L.

TABLE 58

Epinephrine Formulations for Rabbit Dosing

| | Formulation | | | | |
|---|---|---|---|---|---|
| | #R1 | #R2 | #R3 | #R4 | #R5 |
| Epinephrine base | 0 | 0.006 | 3.025 | 3.243 | 3.243 |
| Dilute Hydrochloric Acid 0.5N | 0.3 | 0.5 | 33.27 | 36.2 | 36.2 |
| Dehydrated Alcohol | | | | 40 | 40 |
| Menthol | | | | 1 | 1 |
| Sucralose | 0.5 | | 0.5 | 0.5 | 0.5 |
| Propylene Glycol | | | | 5 | 5 |
| Sodium Bisulfite | 0.2 | 0.01 | 0.2 | 0.3 | 0.3 |
| Edetate Disodium (EDTA) | 0.05 | | 0.05 | 0.05 | 0.05 |
| Water USP | 98.45 | 98.584 | 62.455 | 13.707 | 13.707 |
| Total | 100 | 100 | 100 | 100 | 100 |

Components: % w/w

TABLE 59

Additional Epinephrine Formulations for Rabbit Dosing

| | Formulation | | |
|---|---|---|---|
| | #R6 | #R7 | #R8 |
| Epinephrine base | 6.648 | 12.88 | 12.88 |
| Dilute Hydrochloric Acid 1.5N | 24.6 | | |
| Dilute Hydrochloric Acid 3N | | 24.2 | 24.2 |
| Dehydrated Alcohol | 40 | 40 | 40 |
| Menthol | 0.5 | 0.5 | 0.5 |
| Sucralose | 0.5 | 0.5 | 0.5 |
| Propylene Glycol | 5 | 5 | 5 |
| Sodium Bisulfite | 0.6 | 0.6 | 0.6 |
| Edetate Disodium (EDTA) | 0.1 | 0.1 | 0.1 |
| Water USP | 21.552 | 15.72 | 15.72 |
| Caprylic acid | 0.5 | | |
| Capric acid | | | 0.5 |
| Total | 100 | 100 | 100 |

Components: % w/w

TABLE 60

Plasma concentrations for epinephrine after administration to rabbits under fasted conditions.

| | Formulation | | | | |
|---|---|---|---|---|---|
| | #R1 | #R2 | #R3 | #R4 | #R5 |
| Route of administration | SL | IM | SL | SL | SL |
| Dose per animal (mg) | 0 | 0.03 | 3 | 3 | 6 |
| Concentration @ 5 min (ng/mL) | 0.020 | 0.99 | 0.28 | 0.19 | 0.11 |
| Concentration @ 10 min (ng/mL) | 0.011 | 0.83 | 0.24 | 0.32 | 0.35 |
| Concentration @ 15 min (ng/mL) | 0.014 | 0.79 | 0.49 | 0.55 | 0.86 |
| Concentration @ 30 min (ng/mL) | 0.012 | 0.73 | 0.44 | 1.24 | 1.94 |
| $T_{max}$ (min) | 300 | 15 | 240 | 90 | 90 |
| $C_{max}$ (ng/mL) | 0.05 | 1.1 | 1.3 | 2.9 | 6.3 |
| $AUC_{0-24\ h}$ (ng * min/mL) | 6.7 | 96.7 | 217.0 | 537.1 | 956.8 |

Plasma concentration: mean
$T_{max}$: median value
$C_{max}$ and $AUC_{0-24\ h}$: geometric mean
IM denotes intramuscular,
SL denotes sublingual

TABLE 61

Plasma concentrations for epinephrine after administration to rabbits under fasted conditions.

| | Formulation | | | |
|---|---|---|---|---|
| | #R6 | #R7 | #R8 | #R9 |
| Route of administration | SL | SL | SL | SL |
| Dose per animal (mg) | 6 | 12 | 12 | 12 |
| Concentration @ 5 min (ng/mL) | 0.71 | 0.28 | 0.12 | 0.81 |
| Concentration @ 10 min (ng/mL) | 0.37 | 0.46 | 0.17 | 1.10 |
| Concentration @ 15 min (ng/mL) | 0.51 | 0.83 | 0.53 | 1.40 |
| Concentration @ 30 min (ng/mL) | 0.93 | 2.75 | 3.34 | 3.57 |
| $T_{max}$ (min) | 120 | 120 | 180 | 65 |
| $C_{max}$ (ng/mL) | 3.1 | 6.0 | 14.3 | 7.0 |
| $AUC_{0-24\ h}$ (ng * min/mL) | 482.2 | 867.0 | 2145.1 | 1050.1 |

Plasma concentration: mean
$T_{max}$: median value
$C_{max}$ and $AUC_{0-24\ h}$: geometric mean

Example 8. Intranasal Administration of Epinephrine Spray Formulations

Methods

TABLE 62

Clinical Formulations

| | Formulation | |
|---|---|---|
| | #C1 | #C2 |
| Epinephrine Base | 2.962 | 3.178 |
| Hydrochloric Acid 0.5N | 32.93 | 35.471 |
| Edetate Disodium Dihydrate | 0.05 | 0.05 |
| Sodium Bisulfite | 0.15 | 0.15 |
| Benzalkonium Chloride | 0.01 | 0.01 |
| Dehydrated alcohol | — | 40 |
| Sodium Chloride | 0.6 | — |
| Water | 63.298 | 16.141 |

Components: % w/w

Protocol design was a Phase I, proof-of-concept, single-dose open-label, 5-treatment, crossover study to assess the bioavailability of intranasal formulations in adults with seasonal allergies. The study assessed the bioavailability of a single dose 3 milligrams and 6 milligrams dose of epinephrine in a formulation of the present invention to a single 0.3 milligram intramuscular dose of epinephrine via an EpiPen® (0.3 milligrams epinephrine, 1.8 milligrams sodium chloride, 0.5 milligrams sodium metabisulfite, hydrochloric acid to adjust pH, and water for injection). 50 subjects were randomly assigned to one of five groups including 3 milligram intranasal dose of an aqueous formulation of the present invention, 3 milligram intranasal dose of a hydro-alcoholic formulation of the present invention, 6 milligram intranasal dose of an aqueous formulation of the present invention, 6 milligram intranasal dose of a hydro-alcoholic formulation of the present invention and a 0.3 milligram intramuscular dose administered over 4 periods with periods 1 and 2 administered in the absence of allergen and periods 3 and 4 in the presence of an allergen that caused seasonal allergies in the subject. Plasma concentrations were taken at −60, −30, 0, 1, 3, 5, 10, 15, 20, 30, 40, 50, 60, 75, 90, 120, 180, 240 and 360 minutes post-dose.

Results

TABLE 63

Pharmacokinetic profile prior to allergen exposure

| Formulation | $T_{max}$ (Mean) | $C_{max}$ (pg/mL) | $AUC_{last}$ (h * pg/mL) | $AUC_{inf}$ (h * pg/mL) |
|---|---|---|---|---|
| Aqueous | 0.376 (0.05-1.25) | Mean 256 (23.4-1260) GeoMean 149 | Mean 231 (31.4-958) GeoMean 153 | Mean 377 (37.9-1860) GeoMean 206 |
| Hydro-alcoholic | 0.41 (0.05-2.0) | Mean 419 (77.6-1110) GeoMean 314 | Mean 596 (30.7-3520) GeoMean 317 | Mean 727 (31.2-4150) GeoMean 385 |
| Epipen ® | 0.281 (0.05-0.833) | Mean 511 (148-1160) GeoMean 429 | Mean 307 (89.1-698) GeoMean 255 | Mean 329 (91.4-749) GeoMean 273 |

TABLE 64

Pharmacokinetic profile after allergen exposure

| Formulation | $T_{max}$ (Mean) | $C_{max}$ (pg/mL) | $AUC_{last}$ (h * pg/mL) | $AUC_{inf}$ (h * pg/mL) |
|---|---|---|---|---|
| Aqueous | 0.13 (0.017-0.667) | Mean 418(78.5-1900). GeoMean 268 | Mean 231 (76.1-573). GeoMean 197 | Mean 273 (94.9-620). GeoMean 237 |
| Hydro-alcoholic | 0.12 (0.017-0.667) | Mean 639(60.6-3150). GeoMean 447 | Mean 429 (51.8-963). GeoMean- | Mean 497 (52-1100). GeoMean 376 |
| Epipen ® | 0.225 (0.05-0.667) | Mean 649(201-1750). GeoMean 517 | Mean 317(125-557). GeoMean 286 | Mean 362 (166-706). GeoMean 326 |

TABLE 65

Early Epinephrine plasma concentrations

| | Time (Minutes) | Mean (Min-Max) pg/ml |
|---|---|---|
| Before Allergen Exposure | | |
| Aqueous | 1 | 47.8 (0-264) |
| | 3 | 154 (0-749) |
| | 5 | 171 (9.17-844) |
| | 10 | 198 (9.37-1260) |
| Hydro-alcoholic | 1 | 84 (0-353) |
| | 3 | 244 (6.73-933) |
| | 5 | 250 (2.13-1030) |
| | 10 | 200 (34.5-718) |
| After Allergen Exposure | | |
| Aqueous | 1 | 174 (1.77-1390) |
| | 3 | 353 (28.2-1900) |
| | 5 | 288 (31.3-1040) |
| | 10 | 183 (36.2-461) |
| Hydro-alcoholic | 1 | 290 (10.5-1300) |
| | 3 | 581 (42.3-3150) |
| | 5 | 398 (43.5-1340) |
| | 10 | 257 (20.6-692) |

Figure 2:
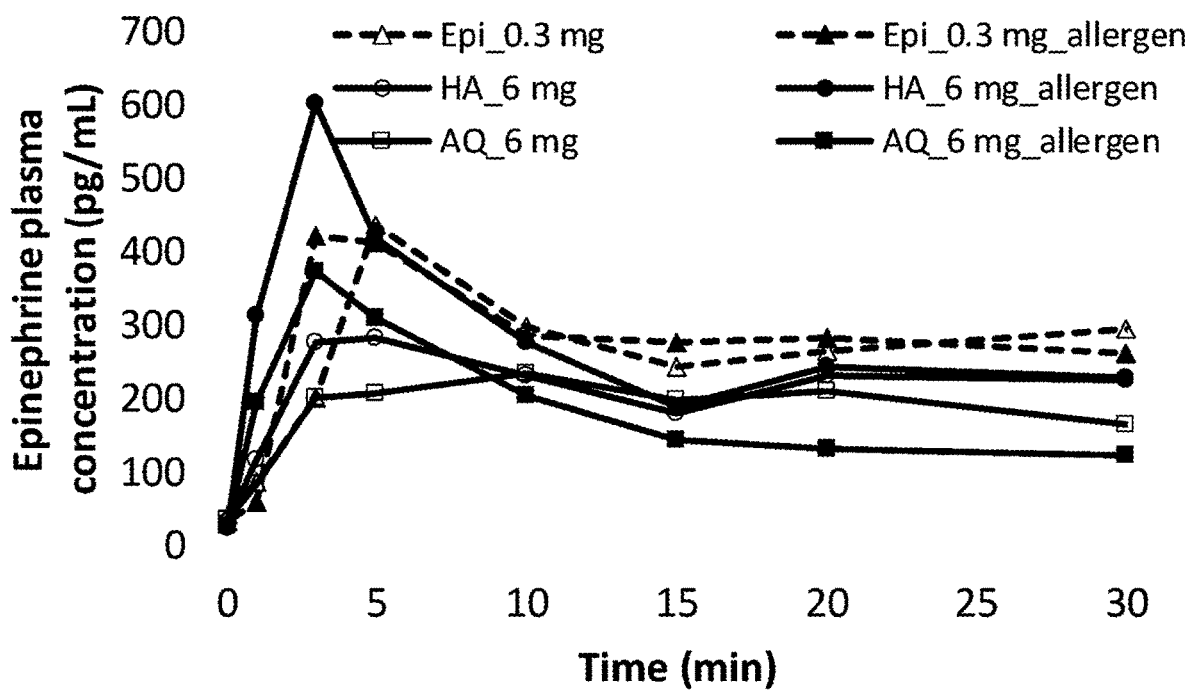
FIG. 2. Epinephrine plasma concentrations over first 30 minutes post administration.
Figure 3:
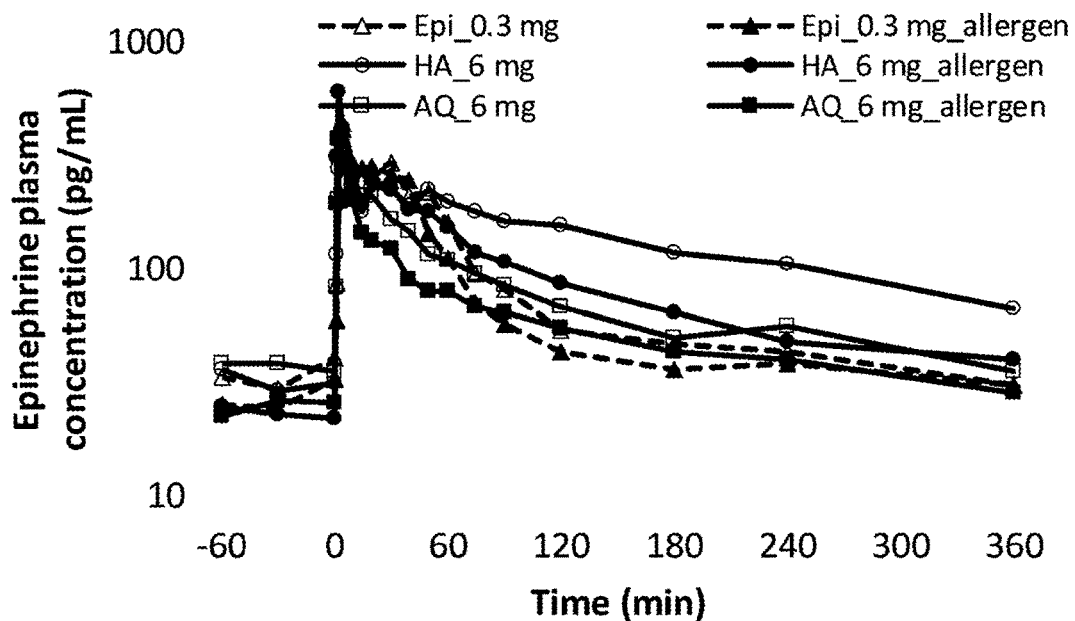
FIG. 3. Semi-log plot of epinephrine plasma concentrations over first 6 hours post administration.
Figure 4:
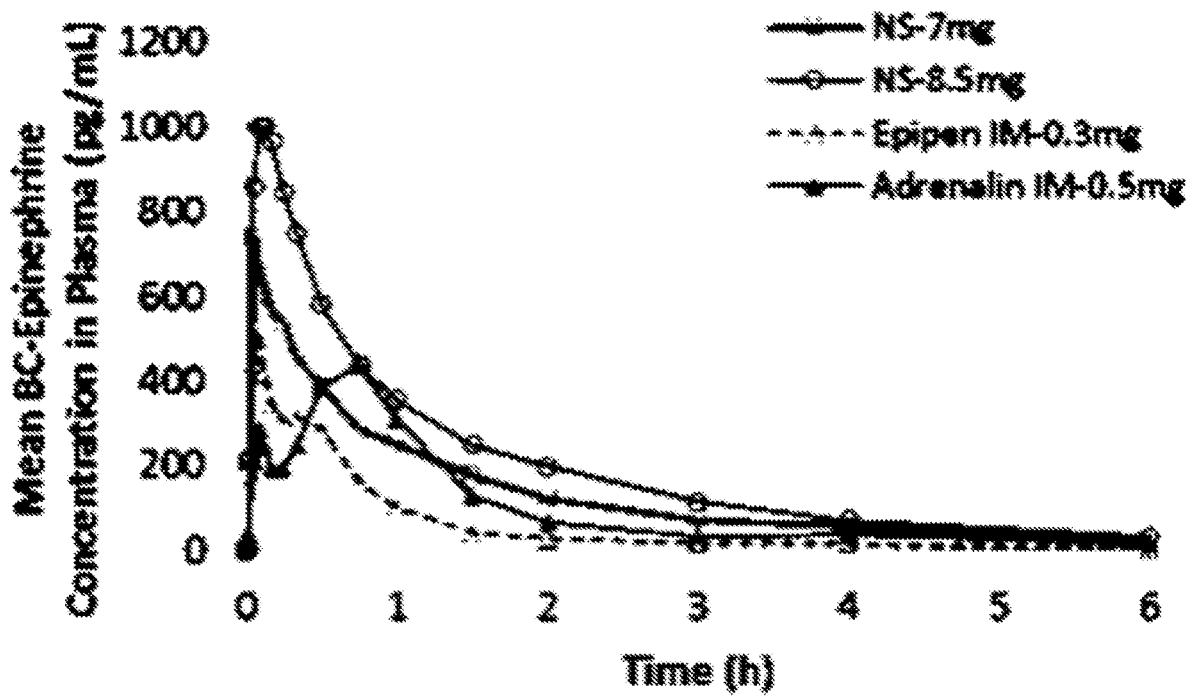
FIG. 4. Epinephrine plasma concentrations over first 6 hours post administration.
Figure 5:
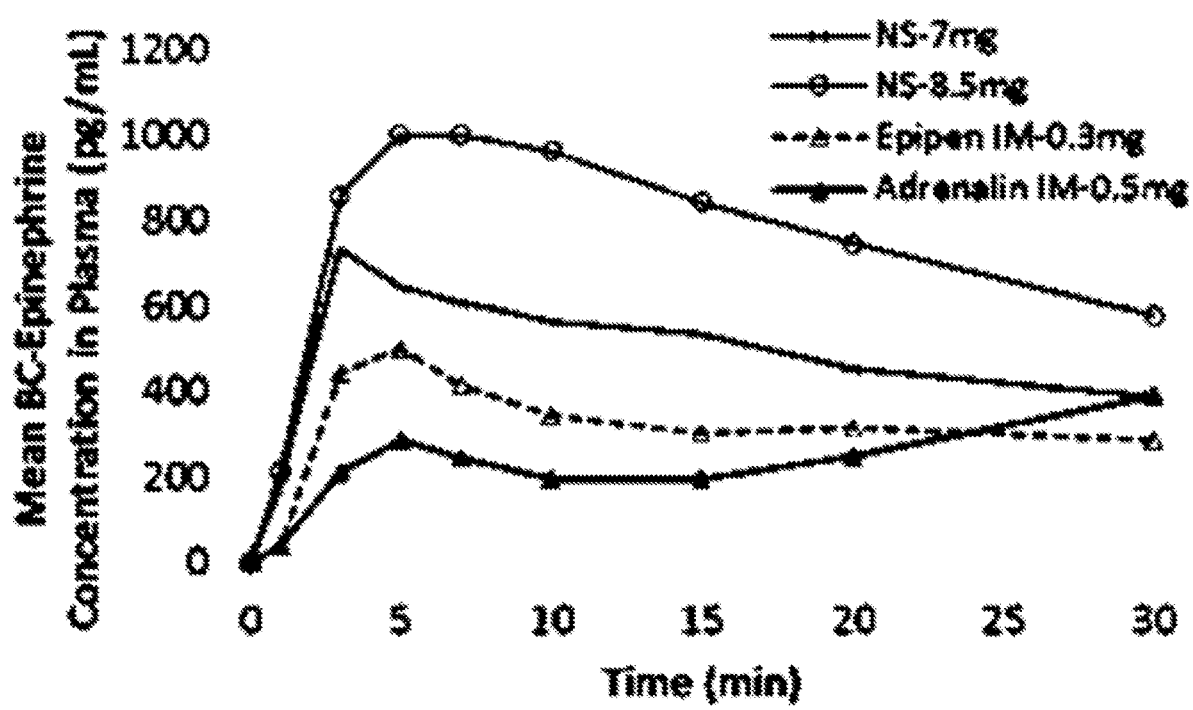
FIG. 5. Epinephrine plasma concentrations over first 30 minutes post administration.

As seen in Tables 63-65 and FIGS. 1-3, subjects administered 6 milligrams of epinephrine in a hydroalcoholic formulation of the present invention in the presence of an allergen had a higher $C_{max}$ than all other cohorts. Further, as seen in FIGS. 1-3, subjects administered 0.3 milligrams of epinephrine as an intramuscular injection in absence of an allergen had a higher $C_{max}$ than all other cohorts in the absence of an allergen. Among subjects receiving either the aqueous or the hydroalcoholic formulations the subjects receiving the hydroalcoholic formulations had a higher $C_{max}$ across the entire sampling time than those receiving the aqueous formulation both in the absence and presence of an allergen. Epinephrine plasma concentrations were greater than 100 pg/mL up to 30 min post dose for all formulations. Further, epinephrine plasma concentration were greater than 100 pg/mL in less than 5 minutes post dose for all formulations of the present invention regardless of exposure to an allergen. Subjects administered the hydroalcoholic formulation had higher exposure in the entire sampling times for up to 6 hours compared to the aqueous formulation.

In conclusion, the bioavailability of intranasal formulations of the present invention is as good or better than that of the intramuscular injection both in subject that are and are not experiencing seasonal allergies.

Example 9. Comparison of Intranasal Formulations of the Invention with Epipen® and IM Adrenalin Methods This was a single-dose, open-label, randomized, four-treatment, four-way crossover study to assess the pharmacokinetics of two test formulations of hydro-alcoholic Epinephrine Nasal Spray containing 7 mg (2 sprays of Composition #37) and 8.5 mg (2 sprays of Composition #38) epinephrine in comparison with reference formulations of Epinephrine IM Injection, EpiPen® (0.30 mg administered intra muscularly), and Epinephrine IM Injection, Adrenalin® (0.50 mg administered intramuscularly; Adrenalin® contains 1.0 milligrams epinephrine, 6.15 milligrams sodium chloride, 0.457 milligrams sodium metabisulfite, 0.920 milligrams sodium hydroxide, 2.25 milligrams tartaric acid, 0.20 milligrams disodium edetate dihydrate, hydrochloric acid to adjust pH, milligrams chlorobutanol and water for injection). Each dose of study treatment was separated by a washout period of 24 hours. Healthy volunteer subjects received hydro-alcoholic Epinephrine Nasal Spray (7 mg and 8.5 mg) and Epinephrine IM Injection (EpiPen® [0.30 mg] and Adrenalin® [0.50 mg]), following an overnight fast of at least 10 hours.

This study consisted of five periods: a Screening Period and four Treatment Periods. During screening (Day -28 to Day -1), subjects signed the informed consent and then underwent determination of eligibility. Based on successful completion of the screening process, approximately 48 subjects were enrolled. Subjects received a single dose of each test formulation and a single dose of each reference formulation administered on Day 1 Period 1, Day 2 Period 2, Day 3 Period 3, and Day 4 Period 4, depending upon treatment sequence assignment. Subjects were confined before dosing to ensure adherence to the 10 hour fast and remained confined until all study procedures are completed on Day 5. No food was allowed until at least 4 hours after each dose administration. No water was consumed from 1 hour prior until 1 hour after each dose administration. Meals were provided at scheduled times. Blood samples for pharmacokinetic (PK) analyses was collected prior to and at multiple times following each dose of study drug. Safety and tolerability was assessed throughout the study.

Pharmacokinetics:

Sampling times: A total of 288 mL (72×4 mL samples) of blood was collected for pharmacokinetic analysis from each subject. Blood samples (1×4 mL) for epinephrine analysis was collected in Vacutainer tubes containing $K_2$-EDTA as a preservative at −60 and −30 minutes, 0 hour (pre-dose), 1, 3, 5, 7, 10, 15, 20, 30, and 45 minutes; and at 1, 1.5, 2, 3, 4, and 6 hours post dose (18 time points) in each study period. The pre-dose blood sample was collected within 60 minutes prior to each dose of study drug.

Bioanalytical method: Plasma concentrations of epinephrine was analyzed using a validated liquid chromatography coupled with tandem mass spectrometry (LC/MS/MS) assay with a lower limit of quantification (LLOQ) of 10.0 pg/mL.

PK parameters: Plasma concentrations of epinephrine (with and without baseline-correction) were used to determine the following PK parameters using noncompartmental PK analysis (NCA):

1. Maximum plasma concentration observed ($C_{max}$),
2. Time to reach maximum plasma concentration ($t_{max}$),
3. Area under the curve from time 0 to the last measured concentration ($AUC_{last}$),
4. Area under the curve extrapolated to infinity ($AUC_{0-inf}$),
5. The time prior to the first measurable (non-zero) concentration ($t_{lag}$),
6. Terminal elimination half-life ($t_{1/2}$),
7. The last quantifiable concentration (Clast), and time corresponding this concentration ($t_{last}$),
8. Apparent total body clearance after extravascular administration (CL/F),
9. Apparent volume of distribution in the terminal phase (Vz/F), and
10. Relative bioavailability of epinephrine for test formulation compared to reference formulation (Frel).

Baseline-correction was performed by subtracting the mean of epinephrine concentrations at −1, −0.5, and 0 h from each post-dose concentration. Baseline-corrected concentrations that are less than 0 will be set to 0 pg/mL.

Results

TABLE 66

Mean plasma concentration after administration of nasal compositions #37 and #38, Epipen ® and intramuscular adrenalin

| | BC-Mean Plasma Conc | | | | | | | |
|---|---|---|---|---|---|---|---|---|
| | Composition #37 (7.0 mg) | | Composition #38 (8.5 mg) | | Epipen ® IM (0.3 mg) | | Adrenalin IM (0.5 mg) | |
| h | Mean | CV (%) | Mean | CV (%) | Mean | CV (%) | Mean | CV (%) |
| 0.0000 | 0 | 0 | 0 | 0 | 0 | 0 | 0 | 0 |
| 0.0167 | 176 | 147 | 217 | 188 | 41.2 | 131 | 39.6 | 177 |
| 0.0500 | 768 | 178 | 860 | 187 | 444 | 143 | 222 | 158 |
| 0.0833 | 663 | 167 | 1020 | 189 | 502 | 86.6 | 288 | 110 |
| 0.1167 | 623 | 158 | 1000 | 188 | 416 | 78.7 | 246 | 87.8 |
| 0.1667 | 566 | 157 | 965 | 193 | 346 | 98.6 | 196 | 70.8 |
| 0.2500 | 535 | 142 | 863 | 156 | 303 | 63.5 | 197 | 75.4 |
| 0.3333 | 455 | 129 | 749 | 131 | 314 | 50.1 | 251 | 73.3 |
| 0.5000 | 389 | 105 | 580 | 104 | 288 | 45.6 | 391 | 65.9 |
| 0.7500 | 283 | 95.8 | 440 | 99.0 | 164 | 56.7 | 438 | 59.9 |
| 1.0 | 251 | 108 | 356 | 98.0 | 104 | 57.9 | 310 | 48.1 |
| 1.5 | 175 | 109 | 249 | 81.8 | 44.1 | 76.2 | 130 | 58.9 |
| 2.0 | 123 | 97.0 | 199 | 85.7 | 30.7 | 79.8 | 65.8 | 54.0 |
| 3.0 | 73.8 | 90.2 | 117 | 79.2 | 17.7 | 103 | 34.4 | 66.6 |
| 4.0 | 54.6 | 140 | 72.0 | 94.5 | 18.1 | 93.8 | 37.3 | 68.7 |
| 6.0 | 14.5 | 176 | 33.3 | 113 | 6.10 | 156 | 18.3 | 87.6 |

TABLE 67

Pharmacokinetic parameters after administration of nasal compositions #37 and #38, Epipen ® and intramuscular adrenalin

| | Composition #37 (7.0 mg) | Composition #38 (8.5 mg) | Epipen ® IM (0.3 mg) | Adrenalin IM (0.5 mg) |
|---|---|---|---|---|
| N | 48 | 49 | 49 | 49 |
| $C_{max}$ (pg/mL) | 1040 ± 1380 | 1420 ± 2080 | 768 ± 585 | 602 ± 326 |
| | (133) [536] | (146) [686] | (76.2) [617] | (54.1) [531] |
| $t_{max}^{b}$ (h) | 0.167 (0.0167-4.0) | 0.267 (0.0167-3.0) | 0.0833 (0.05-1.0) | 0.550 (0.05-1.0) |
| $AUC_{last}$ (pg · h/mL) | 785 ± 795 | 1200 ± 1040 | 357 ± 119 | 598 ± 229 |
| | (101) [521] | (86.7) [813] | (33.4) [338] | (38.3) [555] |
| $AUC_{0-inf}$ (pg · h/mL) | 960 ± 594 | 1440 ± 1160 | 365 ± 118 | 685 ± 281 |
| | (61.9) [828] | (80.6) [1030] | (32.3) [346] | (41.0) [627] |
| $t_{1/2}$ (h) | 1.20 ± 0.542 | 1.51 ± 0.914 | 0.979 ± 0.586 | 1.99 ± 1.76 |
| | (45.3) [1.09] | (60.7) [1.31] | (59.9) [0.833] | (88.3) [1.37] |

Note:
$C_{max}$, AUC and $t_{1/2}$ values represent Mean ± SD (CV) [GeoMean]

TABLE 68

Baseline-adjusted Epinephrine Plasma Concentrations and Their Ratios to EpiPen ® 0.3 mg IM Injection at Early Times Through 60 Minutes Post-dose

| Time in Minutes | Compositions #37 (7.0 mg) [N = 48] | | Composition #38 (8.5 mg) [N = 49] | | EpiPen ® 0.3 mg IM Injection [N = 49] | Adrenalin ® 0.5 mg IM Injection (N = 49) | |
|---|---|---|---|---|---|---|---|
| | Conc* | Ratio to EpiPen | Conc* | Ratio to EpiPen | Conc* | Conc* | Ratio to EpiPen |
| 1  | 176 (147)  | 4.3 | 217 (188)  | 5.3 | 41.2 (131) | 39.6 (177)  | 1.0 |
| 3  | 768 (178)  | 1.7 | 860 (187)  | 1.9 | 444 (143)  | 222 (158)   | 0.5 |
| 5  | 663 (167)  | 1.3 | 1020 (189) | 2   | 502 (86.6) | 288 (110)   | 0.6 |
| 7  | 623 (158)  | 1.5 | 1000 (188) | 2.4 | 416 (78.7) | 246 (87.8)  | 0.6 |
| 10 | 566 (157)  | 1.6 | 965 (193)  | 2.8 | 346 (98.6) | 196 (70.8)  | 0.6 |
| 15 | 535 (142)  | 1.8 | 863 (156)  | 2.8 | 303 (63.5) | 197 (75.4)  | 0.7 |
| 20 | 455 (129)  | 1.4 | 749 (131)  | 2.4 | 314 (50.1) | 251 (73.3)  | 0.8 |
| 30 | 389 (105)  | 1.4 | 580 (104)  | 2   | 288        | 391 (65.9)  | 1.4 |
| 45 | 283 (95.8) | 1.7 | 440 (99.0) | 2.7 | 164 (56.7) | 438 (59.9)  | 2.7 |
| 60 | 251 (108)  | 2.4 | 356 (98.0) | 3.4 | 104 (57.9) | 310 (48.13) | 3   |

*Mean (CV %) plasma concentration in pg/Ml
Conc = Concentration

TABLE 69

Epinephrine Baseline-Adjusted Partial Areas Under the Plasma Epinephrine Concentration Versus Time Curve and Their Ratios to EpiPen 0.3 mg IM Injection at Early Times Through 60 Minutes Post-dose

| | Compositions #37 (7.0 mg) [N = 48] | | Composition #38 (8.5 mg) [N = 49] | | EpiPen ® 0.3 mg IM Injection [N = 49] | Adrenalin ® 0.5 mg IM Injection (N = 49) | |
|---|---|---|---|---|---|---|---|
| | AUC* | Ratio to EpiPen | AUC* | Ratio to EpiPen | AUC* | AUC* | Ratio to EpiPen |
| $AUC_{0-0.017}$ | 1.50 (150)  | 4.2 | 1.80 (195)  | 5   | 0.358 (130) | 0.324 (180) | 0.9 |
| $AUC_{0-0.05}$  | 16.8 (153)  | 2   | 19.1 (182)  | 2.3 | 8.44 (131)  | 4.54 (141)  | 0.5 |
| $AUC_{0-0.083}$ | 39.8 (163)  | 1.7 | 49.8 (180)  | 2.1 | 23.9 (112)  | 12.8 (129)  | 0.5 |
| $AUC_{0-0.117}$ | 61.1 (161.0)| 1.6 | 83.9 (179)  | 2.1 | 39.3 (94.1) | 21.8 (113)  | 0.6 |
| $AUC_{0-0.167}$ | 90.4 (156)  | 1.6 | 133 (180)   | 2.3 | 58.1 (82)   | 32.7 (98.6) | 0.6 |
| $AUC_{0-0.25}$  | 136 (148)   | 1.6 | 208 (176.0) | 2.5 | 84.7 (72.3) | 48.8 (85.6) | 0.6 |
| $AUC_{0-0.33}$  | 175 (143)   | 1.6 | 272 (167)   | 2.5 | 109 (64)    | 66.4 (77.4) | 0.6 |
| $AUC_{0-0.5}$   | 246 (132.0) | 1.5 | 386 (147)   | 2.4 | 160 (51.0)  | 120 (65.6)  | 0.8 |
| $AUC_{0-0.75}$  | 329 (120)   | 1.5 | 513 (129)   | 2.4 | 214 (42.2)  | 223 (57.6)  | 1   |
| $AUC_{0-1}$     | 395 (112)   | 1.6 | 611 (120)   | 2.5 | 247 (38.7)  | 315 (50.5)  | 1.3 |

*Mean (CV %) area under the curve (AUC) between time 0 and t, h*pg/mL

As can be seen in Table 66, intranasal administration of compositions #37 and #38 resulted in higher plasma concentrations 5 minutes (0.0833 hours) after administration than either Epipen® or intramuscular adrenalin. In fact, the 8.5 mg dose of composition #38 resulted in more than twice the plasma concentration of either Epipen® or intramuscular adrenalin. Plasma concentrations of epinephrine remained higher in subjects administered compositions #37 or #38 than Epipen® or intramuscular adrenalin for 6 hours following administration.

As can be seen in Table 67, intranasal administration of compositions #37 and #38 resulted in higher $C_{max}$, $AUC_{last}$ and $AUC_{0-inf}$ than either Epipen® or intramuscular adrenalin. In fact, administration of compositions #37 and #38 resulted in 1.4 and 1.8 times greater $C_{max}$ than Epipen®.

As seen in Table 68, intranasal administration of compositions #37 and #38 resulted in much higher ratios of epinephrine plasma concentrations compared to EpiPen® than did Adrenalin® IM injections. In fact, administration of compositions #37 and #38 resulted in 4.3- and 5.3-times higher epinephrine plasma concentration after 1 minute compared to EpiPen®.

As seen in Table 69, intranasal administration of compositions #37 and #38 resulted in much higher ratios of epinephrine AUC compared to EpiPen® than did Adrenalin® IM injections. In fact, administration of compositions #37 and #38 resulted in 4.2- and 5-times higher epinephrine AUC after 1 minute compared to EpiPen®.

What we claim is:

1. An epinephrine spray formulation comprising:
   from about 3% to about 5% w/w epinephrine base;
   from about 20% to about 25% w/w hydrochloric acid with a normality of about 1.0N;
   from about 35% to about 45% w/w ethanol;
   from about 2.5% to about 7.5% w/w propylene glycol; and
   from about 20% to about 40% w/w water.

2. An epinephrine spray formulation comprising:
   about 3.885% w/w epinephrine base;
   about 21.681% w/w hydrochloric acid with a normality of about 1.0N;
   about 0.05% w/w edetate disodium dihydrate;
   about 0.184% w/w sodium bisulfite;
   about 0.01% w/w benzalkonium chloride;

about 40.0% w/w ethanol;
about 5.0% w/w propylene glycol; and
about 29.190% w/w water.

3. An epinephrine spray formulation comprising:
from about 3% to about 6% w/w epinephrine base;
from about 20% to about 30% w/w hydrochloric acid with a normality of about 1.0N;
from about 35% to about 45% w/w ethanol;
from about 2.5% to about 7.5% w/w propylene glycol; and
from about 20% to about 30% w/w water.

4. An epinephrine spray formulation comprising:
about 4.702% w/w epinephrine base;
about 26.241% w/w hydrochloric acid with a normality of about 1.0N;
about 0.05% w/w edetate disodium dihydrate;
about 0.223% w/w sodium bisulfite;
about 0.01% w/w benzalkonium chloride;
about 40.0% w/w ethanol;
about 5.0% w/w propylene glycol; and
about 23.774% w/w water.

\* \* \* \* \*